US012608789B2

(12) United States Patent
Goodwin et al.

(10) Patent No.: US 12,608,789 B2
(45) Date of Patent: Apr. 21, 2026

(54) SYSTEMS AND METHODS FOR AUTOMATED IN-LINE PLUNGER DEPTH MEASUREMENT

(71) Applicant: AMGEN INC., Thousand Oaks, CA (US)

(72) Inventors: Al Patrick Goodwin, Dunleer (IE); Graham F. Milne, Ventura, CA (US); Thomas C. Pearson, Newbury Park, CA (US); Jordan Ray Fine, Ventura, CA (US)

(73) Assignee: AMGEN INC., Thousand Oaks, CA (US)

( * ) Notice: Subject to any disclaimer, the term of this patent is extended or adjusted under 35 U.S.C. 154(b) by 1017 days.

(21) Appl. No.: 17/670,745

(22) Filed: Feb. 14, 2022

(65) Prior Publication Data

US 2022/0261977 A1    Aug. 18, 2022

Related U.S. Application Data

(60) Provisional application No. 63/149,600, filed on Feb. 15, 2021.

(51) Int. Cl.
G06T 7/00        (2017.01)
A61M 5/315        (2006.01)
G06T 7/11        (2017.01)

(52) U.S. Cl.
CPC ......... G06T 7/001 (2013.01); A61M 5/31565 (2013.01); G06T 7/11 (2017.01); G06T 2207/30004 (2013.01)

(58) Field of Classification Search
CPC .............................. G01B 11/14; G01F 11/027
See application file for complete search history.

(56) References Cited

U.S. PATENT DOCUMENTS 4,666,303 A * 5/1987 Pryor ..................... G01B 11/14
356/606
9,881,367 B1 1/2018 Milne et al.
(Continued)

FOREIGN PATENT DOCUMENTS

DE 102011055735 A1 5/2013
EP 2478337 B1 8/2015
(Continued)

OTHER PUBLICATIONS

International Application No. PCT/US2022/016269, International Search Report and Written Opinion, mailed May 23, 2022.

*Primary Examiner* — Uzma Alam
*Assistant Examiner* — Mohamed Doumbia
(74) *Attorney, Agent, or Firm* — MARSHALL, GERSTEIN & BORUN LLP

(57)        ABSTRACT

An automated inspection system includes a sensor system that includes a sensor and is configured to generate a plurality of syringe scans by scanning each of a plurality of syringes. Each of the plurality of syringe scans is indicative of distance relative to the sensor. The automated inspection system also includes one or more processors configured to, for each of the plurality of syringes, analyze the respective syringe scan to determine (i) a first distance to a first portion (e.g., flange) of the syringe and (ii) a second distance to a second portion (e.g., plunger) of the syringe, and calculate a distance between the first and second portions based on the first distance and the second distance.

30 Claims, 20 Drawing Sheets

(56)                    References Cited

U.S. PATENT DOCUMENTS

| | | | |
|---|---|---|---|
| 2005/0030528 A1* | 2/2005 | Geffen | G01B 11/0608 356/609 |
| 2006/0178578 A1 | 8/2006 | Tribble et al. | |
| 2009/0077504 A1* | 3/2009 | Bell | G06F 3/017 715/863 |
| 2012/0268741 A1* | 10/2012 | Pommereau | G01F 23/2921 356/343 |
| 2013/0278927 A1* | 10/2013 | Johnson | G01N 21/9054 356/240.1 |
| 2014/0210981 A1* | 7/2014 | Stauffer | G01B 11/06 348/79 |
| 2019/0056335 A1* | 2/2019 | Grandvuillemin | G01N 21/958 |
| 2020/0070350 A1* | 3/2020 | Thobe | B25J 9/1697 |
| 2021/0215619 A1* | 7/2021 | Shu | G01N 21/8901 |
| 2023/0349837 A1* | 11/2023 | Virot | G02B 21/0064 |

FOREIGN PATENT DOCUMENTS

| | | | | | |
|---|---|---|---|---|---|
| EP | 2885032 | B1 | 1/2018 | | |
| GB | 2337815 | A | 12/1999 | | |
| JP | 2013505433 | A | 2/2013 | | |
| JP | 2015080473 | A | 4/2015 | | |
| JP | 2015529481 | A | 10/2015 | | |
| JP | 2015529505 | A | 10/2015 | | |
| WO | WO-2011032960 | A1 | 3/2011 | | |
| WO | WO-2014009442 | A1 | 1/2014 | | |
| WO | WO-2014029681 | A2 | 2/2014 | | |
| WO | WO-2019032101 | A1 * | 2/2019 | | A61M 5/178 |

* cited by examiner 640-2

640-1

800

1100

1112-6

1118-6

1110

1104

1111B

1102

1119

1118-1

1111A 1112-1

1119

1119-6

1119-1

1119

1119-1

1119-6

1300

| Flange orientation | Sample 1 | Sample 2 | Sample 3 | Sample 4 | Sample 5 | Sample 6 | Sample 7 | Sample 8 | Sample 9 | Sample 10 |
|---|---|---|---|---|---|---|---|---|---|---|
| | 7 | 8.59 | 9.22 | 9.81 | 11.1 | 12 | 13.91 | 14.02 | 15.88 | 16.58 |
| | 7.02 | 8.63 | 9.27 | 9.82 | 11.13 | 12.02 | 13.92 | 14.04 | 15.91 | 16.57 |
| | 7 | 8.62 | 9.2 | 9.82 | 11.15 | 12.01 | 13.89 | 14.04 | 15.83 | 16.57 |
| | 7.01 | 8.63 | 8.23 | 8.81 | 11.15 | 12.01 | 13.92 | 14.12 | 15.84 | 16.59 |
| | 6.99 | 8.61 | 9.22 | 9.82 | 11.13 | 12.03 | 13.91 | 14.02 | 15.85 | 16.55 |
| | 7.01 | 8.61 | 9.26 | 9.82 | 11.14 | 12.04 | 13.91 | 14.04 | 15.89 | 16.56 |
| | 6.98 | 8.6 | 9.24 | 9.83 | 11.14 | 12.03 | 13.91 | 14.02 | 15.91 | 16.58 |
| | 7.01 | 8.64 | 9.24 | 9.82 | 11.15 | 12.03 | 13.91 | 14.02 | 15.9 | 16.58 |
| | 7 | 8.64 | 9.23 | 9.83 | 11.1 | 12.01 | 13.9 | 14.02 | 15.87 | 16.55 |

Plunger Depth in mm (Confocal Chromatic Sensor)

Plunger Depth in mm (Optical Comparator)

SYSTEMS AND METHODS FOR AUTOMATED IN-LINE PLUNGER DEPTH MEASUREMENT

CROSS-REFERENCE TO RELATED APPLICATIONS

This application claims the benefit of U.S. Provisional Patent Application No. 63/149,600, filed on Feb. 15, 2021 and entitled "Systems and Methods for Automated In-Line Plunger Depth Measurement," the entire disclosure of which is hereby incorporated herein by reference.

FIELD OF THE DISCLOSURE

The present application generally relates to quality control techniques, and more specifically relates to techniques for measuring the distance between portions of a syringe (e.g., for measuring the depth of syringe plungers).

BACKGROUND

Rigorous quality control measures are required for the manufacture of various drug products and the vessels that contain those drug products. For fluid-based drugs in syringes, one such quality control measure includes inspecting each syringe to ensure that the plunger (e.g., rubber piston or stopper) is at the proper depth within the syringe barrel. Plunger depth is typically measured as the distance between the top of the syringe flange and the top of the plunger, while the syringe is in an upright position with the needle pointing downward. The plunger depth is typically checked during the fill process and, for combination/auto-injection devices, a second time prior to assembly.

At the point of fill, in-process controls (IPCs) are employed to ensure that settings for the automated fill line are correct, and to ensure that the filling machine is operating in accordance with those settings. For auto-injection devices (e.g., a SureClick® or other combination device), inspection is repeated prior to assembly because the plunger can move/settle after filling and during transport, particularly when the ambient air pressure changes. In auto-injection devices, a plunger depth falling outside of a specified depth range may cause the auto-injector to malfunction or provide an incorrect dosage. For example, if the plunger is positioned too low in the syringe (i.e., towards the needle) the spring-activated piston used by an auto-injector pen may travel a longer distance before contact, thereby gathering excessive kinetic energy. This may produce a shockwave down the glass body of the syringe upon contact with the plunger, resulting in glass breakage near the tapered end of the needle. Plunger position can also impact other quality-related aspects, such as container closure integrity and sterility. Accordingly, for both the fill stage and the assembly stage, it is important that robust processes be used to ensure that plunger positions fall within prescribed specifications.

Traditionally, plunger depth measurements have been manual processes (e.g., using calipers or optical comparators). More recently, automated visual inspection (AVI) solutions have been developed that use machine vision to mitigate the inconsistencies and inefficiencies associated with manual processes. However, these AVI techniques can suffer from their own drawbacks. For example, because plunger depth measurement typically requires a non-destructive and non-contact approach, AVI techniques that have been developed to date measure the plunger depth using a camera that views each syringe through the cylindrical side wall (i.e., orthogonal to the central/long axis of the syringe). This presents a problem when syringes are arranged in certain types of containers (e.g., syringe "tubs"), as is common during and after the fill stage, because the containers prevent imaging from a side perspective. Thus, these AVI techniques generally require that syringes be subject to additional handling (e.g., removed from standard syringe tubs), above and beyond the handling already required for fill and assembly lines. This additional handling can be associated with other drawbacks, such as lower throughput, more costly inspection equipment, increased measurement variance due to tolerances in how each syringe is handled/held, more opportunities for contamination, additional mechanisms that can become points of failure, and so on.

AVI techniques can also be problematic in applications that do not utilize syringe tubs, such as when the syringes are inspected while in Rondo trays, star wheels, or linear assembly lines. In particular, the geometry of the system may not be suitable for integration of side-view cameras, and/or machine vision techniques can introduce image processing delays that cause the plunger depth inspection points to become bottlenecks in the manufacturing process.

BRIEF SUMMARY

To address some of the aforementioned drawbacks of current manual and AVI practices, embodiments described herein employ non-destructive, non-contact measurement techniques that scan syringes using a proximal-end perspective (i.e., facing the ends of the syringes that are opposite to the syringe needles) to inspect syringe plunger depth levels with high accuracy and high throughput. In some embodiments, for example, a scan is generated by scanning syringes using one or more sensors that pass over the proximal ends of upright syringes (i.e., with downward pointing needles), or that use mirrors to redirect the optical path into the proximal ends of the syringes. The sensor may be a sensor with a passive sensor head, such as a confocal chromatic sensor (in which different wavelengths are focused at different distances from the sensor head) or a "single-depth-of-focus" sensor (with a single focal length, and in which the sensor head is moved towards or away from a sample to find or approximate the distance that results in maximum focus), for example. The scan may be a one-dimensional depth profile or a two-dimensional image/array of depth measurements, depending on the sensor scan pattern (e.g., a linear or raster scan). The sensor may generate measurements at a very high rate (e.g., 25,000 to 70,000 per second), and the associated processing can be relatively high-speed/low-complexity (e.g., as compared to machine vision image processing), thereby preventing substantial delays or bottlenecks. Speed may be further increased by arranging multiple sensors in a configuration that permits the sensors to scan different syringes in parallel, or permits different sensors to scan different portions of the same syringe. Moreover, due to the proximal-end perspective of the sensor, plunger depth can be inspected without deviating from the normal handling/conveyance of the syringes (e.g., without removing the syringes from syringe tubs that hold the syringes upright), in some embodiments. This in turn allows for greater flexibility in the design of inspection systems. For example, stand-alone inspection systems employing these techniques (for tub-based systems or otherwise) can be placed virtually anywhere in the production chain. More generally, while the techniques described herein are primarily described with respect to detecting plunger depth (e.g., the distance between the flange and the plunger), these techniques can be applied to determine the distance between any two portions of a syringe, so long as the sensor(s) can individually detect/determine the distance between the sensor (e.g., sensor head) and each of those two portions.

BRIEF DESCRIPTION OF THE DRAWINGS

The skilled artisan will understand that the figures, described herein, are included for purposes of illustration and are not limiting on the present disclosure. The drawings are not necessarily to scale, emphasis instead being placed upon illustrating the principles of the present disclosure. It is to be understood that, in some instances, various aspects of the described implementations may be shown exaggerated or enlarged to facilitate an understanding of the described implementations. In the drawings, like reference characters throughout the various drawings generally refer to functionally similar and/or structurally similar components.

FIG. 13 is a table showing plunger depths calculated for 10 sample syringes across a range of different flange orientations determined using a confocal chromatic sensor.

4

Figure 15:
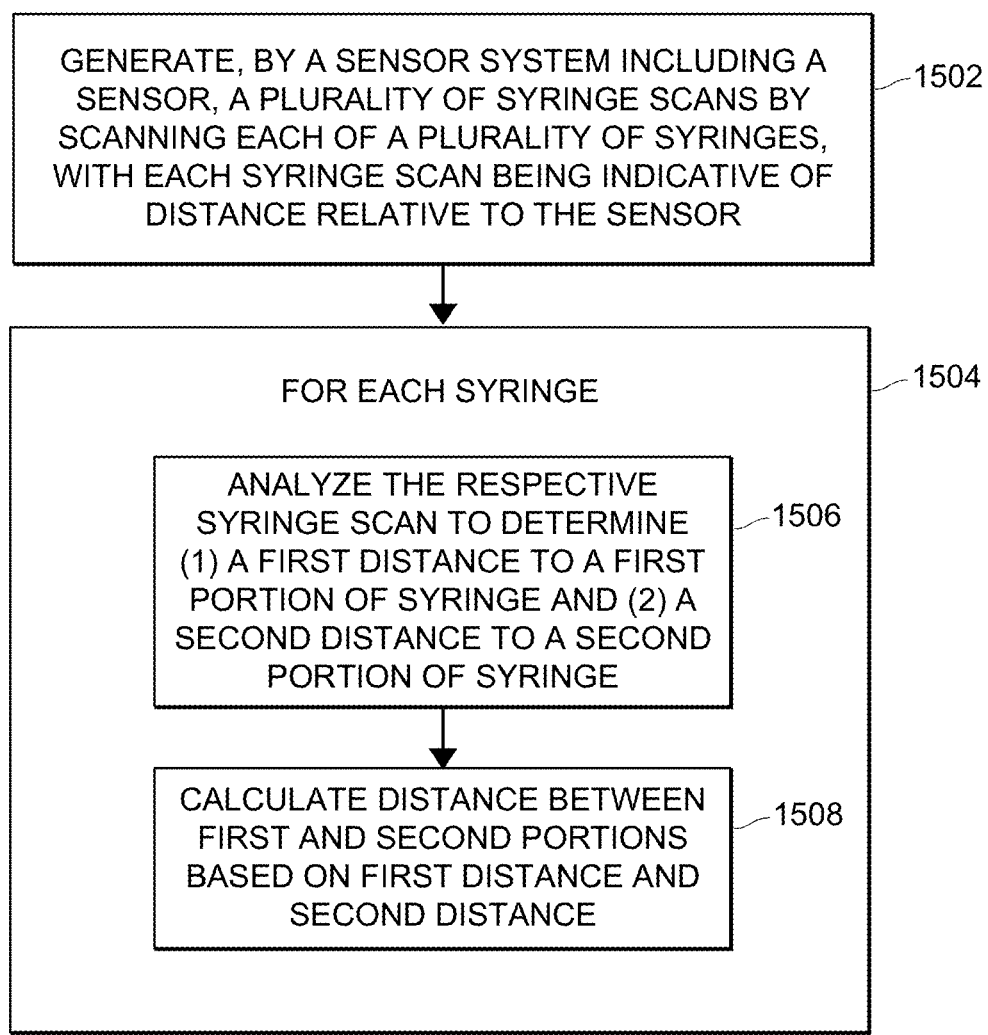

FIG. 15 is a flow diagram of an example method for automated inspection of syringes.

DETAILED DESCRIPTION

The various concepts introduced above and discussed in greater detail below may be implemented in any of numerous ways, and the described concepts are not limited to any particular manner of implementation. Examples of implementations are provided for illustrative purposes.

Figure 1:
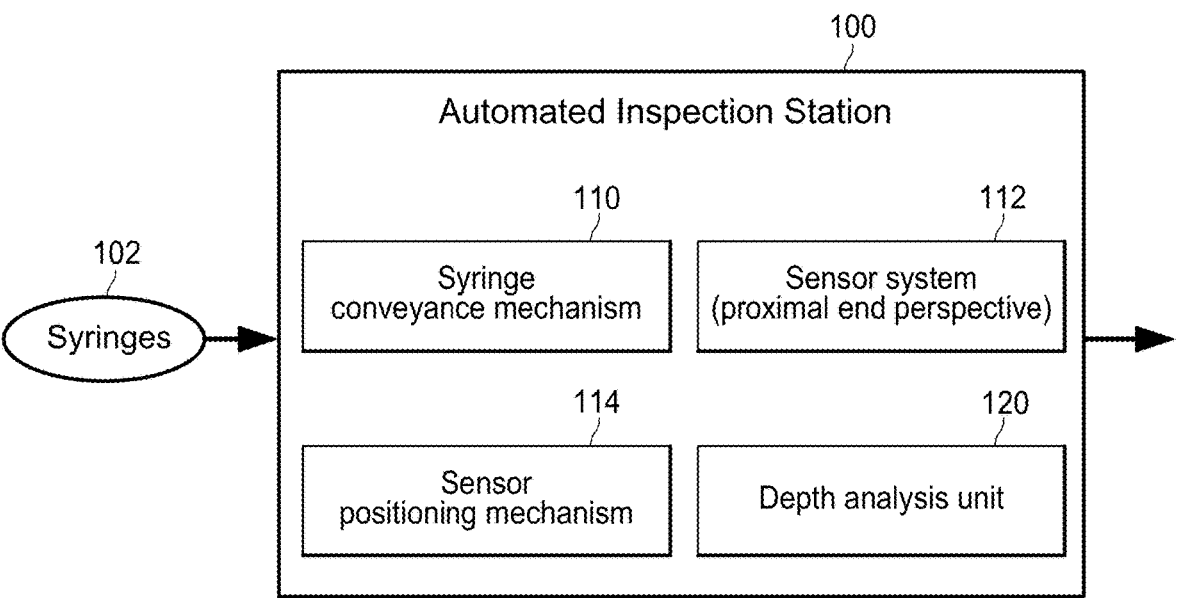
FIG. 1 is a simplified block diagram of an example automated inspection station that can implement syringe depth inspection techniques described herein.
Figure 3:
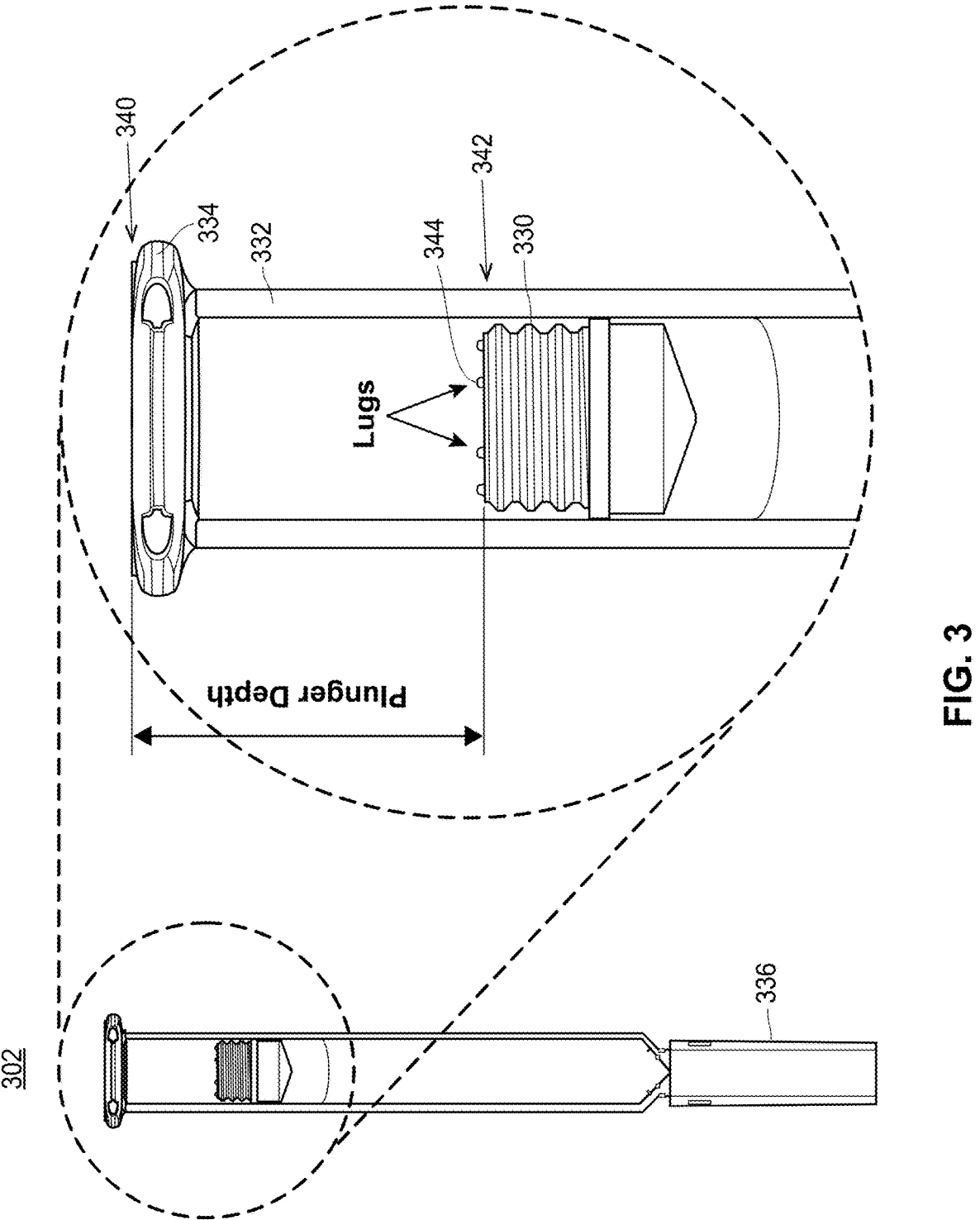
FIG. 3 depicts one way in which plunger depth may be measured.
Figure 4:
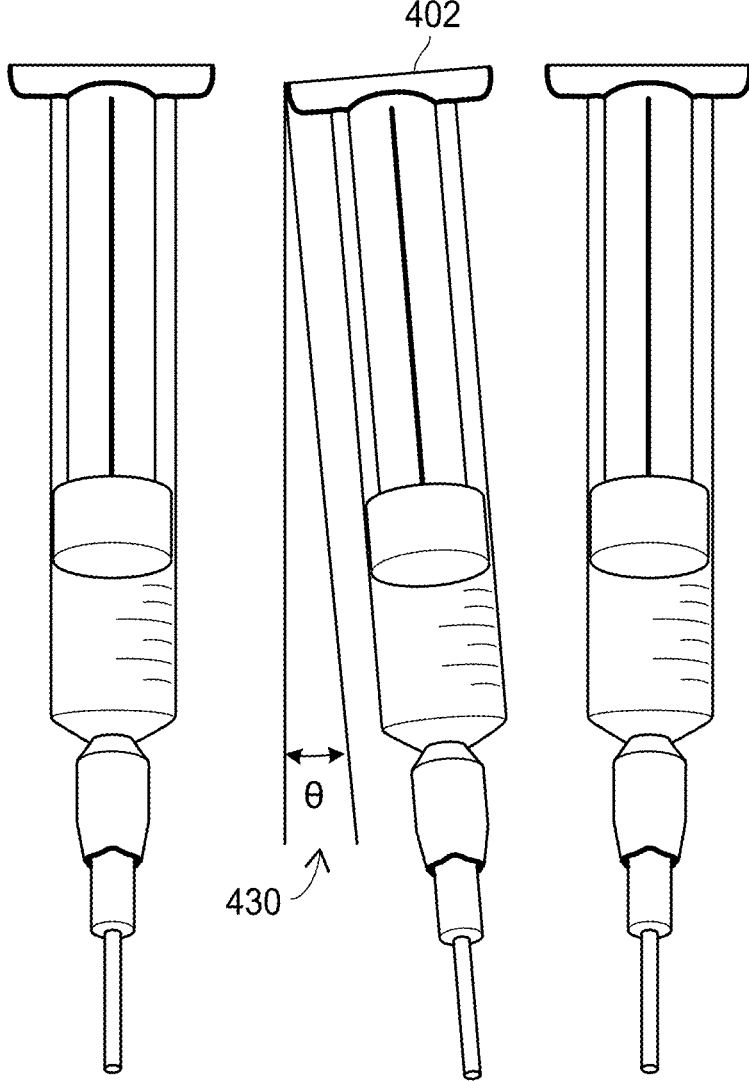
FIG. 4 depicts example orientations in which syringes may be held, including one syringe held with an angular displacement.

FIG. 1 is a simplified block diagram of an example automated inspection station 100 that can inspect syringes 102 for proper plunger depth. More generally, in various embodiments, the automated inspection station 100 may be used to inspect syringes 102 to determine the distance between two portions of each syringe 102. The automated inspection station 100 may be a free-standing station, or may be a single station within line equipment having multiple automated inspection stations (e.g., the automated inspection station 100 plus one or more camera-based, AVI stations for detecting other types of defects), for example. Each of the syringes 102 includes at least a barrel (e.g., cylindrical tube), a plunger (which may also be referred to as a stopper or piston) disposed within the barrel and arranged to move/slide within the barrel, and a flange at a proximal end of the syringe. The syringe also includes a needle or other discharging orifice at the distal end of the syringe. Example syringes are depicted in FIGS. 3-5. The barrel and flange may be constructed of glass (e.g., borosilicate glass), plastic, and/or any other suitable material(s). The plunger may be constructed of rubber, plastic, and/or any other suitable material(s). The needle (or other discharge orifice) may be constructed of metal, plastic, and/or any other suitable material(s). Any of the components of the syringes 102 may be constructed using transparent, semi-transparent, and/or opaque material(s).

In some embodiments, each of the syringes 102 is held within an upright position (e.g., within a syringe tub or Rondo tray, or within individual syringe holders of a star wheel or linear fill or assembly line, etc.). As the term is used herein, an "upright" position of a syringe is one in which the proximal/flange end of the syringe points upward, and the distal/orifice end of the syringe points downward. The syringes 102 may be provided to the automated inspection station 100 by a previous inspection station (e.g., within the same piece of line equipment as the automated inspection station 100), or manually, etc. The automated inspection station 100 includes a syringe conveyance mechanism 110 that accepts the syringes 102 and moves the syringes 102 to a position that is appropriate for scanning. If the syringes 102 are held within a tub or Rondo tray, for example, the syringe conveyance mechanism 110 may include a conveyor belt on which the tub is deposited, and a drive mechanism (e.g., motor) that causes the conveyor belt to move the tub. As another example, if the syringes 102 are not held in a common container, the syringe conveyance mechanism 110 may include the star wheel and a drive motor or pneumatic mechanism that causes the star wheel to rotate by precise increments. As yet another example, the syringe conveyance mechanism 110 may be a linear conveyance mechanism. Various examples of automated inspection stations that may be used as the station 100 are shown in FIGS. 2 and 8-12, which are discussed in further detail below. In some embodiments (e.g., if a tub of syringes 102 is manually positioned within the automated inspection station 100), the automated inspection station 100 does not include the syringe conveyance mechanism 110.

The automated inspection station 100 also includes a sensor system 112 with at least one sensor that, when the syringe conveyance mechanism 110 has positioned the syringes 102 appropriately (or, when the syringes 102 have been manually positioned), scans the syringes 102 from a proximal perspective. That is, the sensor(s) of the sensor system 112 scan the proximal end of each of the syringes 102. If the syringes 102 are in an upright (e.g., needle-down) position, for example, the sensor(s) may be positioned directly above a given syringe when scanning that syringe. The sensor(s) may achieve the proximal perspective directly via positioning of the sensor(s) (i.e., where the optical path between a sensor and a syringe 102 is a straight line), or using an intervening optical system (e.g., where one or more mirrors redirect the optical path between a sensor and a syringe 102, such as the arrangement shown in FIGS. 11A-11D). The sensor system 112 may also include a sensor controller (or possibly one sensor controller per sensor, if the sensor system 112 has multiple sensors), e.g., to convert received/sensed sensor signals to outputs/measurement data that is in a format cognizable to the rest of the system.

Each of the sensor(s) in the sensor system 112 (e.g., each sensor "head") is configured to scan the proximal ends of the syringes 102 in a manner that outputs measurements indicative of depth/distance relative to that sensor. As used herein, it is understood that references to "depth" or "distance" between the sensor and a sample (e.g., a syringe 102 or a portion thereof) can refer to the distance relative to any portion of the sensor (e.g., the sensor head, or a lens system of the sensor head, etc.), and can refer to depth or distance along a straight-line optical path or along an optical path that is redirected one or more times (e.g., via one or more intervening mirrors). In some embodiments, the sensor(s) are passive sensors, such as confocal chromatic sensors. For example, the sensor(s) may be IFS2405-30 sensors from Micro-Epsilon, which can detect about 30 mm of depth range at up to about 70 kHz sampling/measurement rate, and the sensor controller(s) may be confocal DT 2461 controllers from Micro-Epsilon. Alternatively, the sensor(s) may be any other confocal chromatic sensor(s) with sufficient precision, accuracy, sampling rate, and depth range. Confocal chromatic sensors can be advantageous in that they work very well with both transparent and opaque surfaces, making them a good candidate for measuring distances to conventional flanges (e.g., glass flanges) and plungers (e.g., rubber plungers). Confocal chromatic sensors are discussed in further detail below, with reference to FIG. 5A.

In other embodiments, each of the sensor(s) in the sensor system 112 scans the proximal ends of the syringes 102 not only by passing over the syringes, but also by moving closer to and/or further away from the proximal end of each syringe (i.e., to shorten or lengthen the optical path between the sensor and syringe 102, regardless of whether that optical path is a straight line). For example, each of the sensor(s) in the sensor system 112 may be what is referred to herein as a "single-depth-of-focus" sensor. Unlike the confocal chromatic sensor discussed above, the single-depth-of-focus sensor does not separate the light source into its different wavelength components, and thus the sensor is associated with only a single focal length and depth of focus. In these embodiments, a given sensor of the sensor system 112 is moved towards and/or away from the proximal end of a syringe until the distance with the best focus is determined, thereby providing a direct measurement of distance/depth. Single-depth-of-focus sensors are discussed in further detail below, with reference to FIGS. 5B and 5C.

In still other embodiments, the sensor system 112 may instead (or also) include any other suitable type or types of sensors capable of passively or actively sensing depth/distance. For example, the sensor system 112 may include a time-of-flight (ToF) sensor (e.g., range imaging camera) that generates/emits a light (e.g., infrared) signal, and measures the round trip time for the light signal to reflect off a surface (e.g., points along each of the syringes 102) and return to the sensor. For example, a ToF camera may provide 640×480 points of depth, relative to the ToF camera, in a single frame, with a sub-millimeter granularity/precision. The ToF camera may measure time-of-flight for a laser or LED light, for example. As another example, the sensor system 112 may include a triangulation sensor to determine depths. However, various factors may make triangulation sensors unsuitable to plunger depth measurements. For example, triangulation may be impossible for syringes with geometries that prevent large angles of incidence for triangulation (e.g., larger ratios of plunger depth to barrel diameter). Moreover, triangulation sensors typically use red or blue light that do not provide enough reflection from a syringe glass (e.g., borosilicate glass) surface, thereby making it very difficult to obtain a stable measurement. Further still, syringe flange surfaces are often not completely flat, which further increases the difficulty of making triangulation measurements. Unlike triangulation and certain other technologies, the confocal chromatic and single-depth-of-focus sensors discussed herein can detect a borosilicate glass surface (and other likely syringe surfaces, including plunger surfaces) with a reasonably high signal-to-noise ratio.

A sensor positioning mechanism 114 of the automated inspection station 100 moves the sensor(s) of the sensor system 112 relative to the syringes 102 according to a desired scan pattern. The automated inspection station 100 may hold each of the syringes 102 stationary as the sensor positioning mechanism 114 move the sensor(s), thereby reducing the likelihood of undesired syringe movement (e.g., jostling) during the scans. The sensor positioning mechanism 114 may include one or more mounting components to which the sensor(s) of the sensor system 112 are affixed, as well as one or more drive mechanisms (e.g., motors or pneumatic systems) to cause movement of those components in response to electronic control signals. In some embodiments, the sensor positioning mechanism 114 is a three-axis Cartesian robot, such as a TT-C3-4040 robot from Intelligent Actuator, Inc. Cartesian robots can be particularly well suited for embodiments in which the syringes 102 are carried in syringe tubs or similar containers, and generally have suitable levels of precision and reliability of movement. In some embodiments, the sensor positioning mechanism 114 outputs data indicative of the time and/or position (e.g., x-y coordinate) at which each measurement was captured for each of the sensor(s). As discussed below, this information may be used to identify which measurements (e.g., scan portions) correspond to which of the syringes 102.

In some embodiments, the automated inspection station 100 does not include the sensor positioning mechanism 114. For example, the automated inspection station 100 may hold the sensor(s) at fixed position(s) above the syringes 102, as the syringe conveyance mechanism 110 (e.g., star wheel or linear conveyor) passes each syringe past (e.g., under) the sensor(s).

The relative movement between the syringes 102 and the sensor(s), as caused by the sensor positioning mechanism 114 and/or syringe conveyance mechanism 110, results in a particular scan pattern. If a single sensor of the sensor system 112 passes over each of the syringes 102 only once (e.g., in a straight or slightly arced line), for example, the scan pattern is one-dimensional. An example, one-dimensional scan pattern is discussed below with reference to FIG. 6A. In other embodiments, however, the scan pattern may be two-dimensional. An example, two-dimensional scan pattern is discussed below with reference to FIG. 6B. For example, the sensor positioning mechanism 114 may cause a single sensor to perform a raster scan (i.e., multiple, parallel scan lines offset by a fixed distance), a "snake" pattern (e.g., winding back and forth with less abrupt changes in direction at the end of each scan line), a circular scan (e.g., concentric circular scans with different radii), and so on. A snake pattern may be preferred over a raster pattern in order to avoid unnecessary retracement by the sensor. Alternatively, if the sensor system 112 includes two or more sensors having offset positions, a single "pass" of the multiple sensors for a given syringe 102 will result in a two-dimensional pattern (e.g., as discussed below with reference to FIGS. 8A-8C). For any fixed number of sensors used, the optimal scan pattern can be dependent upon the syringe configuration.

The automated inspection station 100 also includes a depth analysis unit 120, which is generally configured to process the measurements generated by the sensor system 112 to determine plunger depths for the syringes 102. The depth analysis unit 120 may include a persistent memory storing instructions, and one or more processors configured to execute the instructions to perform the various operations of the depth analysis unit 120 as discussed herein. Alternatively, one or more of the processors in the depth analysis unit 120 may be other types of processors (e.g., application-specific integrated circuits (ASICs), field-programmable gate arrays (FPGAs), etc.). In various embodiments, the depth analysis unit 120 may be integrated into the same equipment as the rest of the automated inspection station 100, or may be a separate device (e.g., a laptop or desktop computer) communicatively coupled to the rest of the automated inspection station 100.

In some embodiments, the depth analysis unit 120 continuously records the outputs generated by the sensor system 112 as the sensor(s) scan the syringes 102. In other embodiments, the depth analysis unit 120 does not record outputs generated by the sensor system 112, and/or the sensor system 112 does not generate any outputs, in the time intervals when the sensor(s) pass from one syringe 102 to the next syringe 102. Depending on the type of the sensor(s), sensor controller(s) of the sensor system 112 may need to convert each of the sensor measurements into distance/depth measurements in a suitable format. If the sensor(s) include a confocal chromatic sensor, for example, each measurement point of a scan may be a set of amplitudes, each of which represents the amount of reflected light at a different wavelength. A sensor controller of the sensor system 112 (and/or the depth analysis unit 120) then converts each set of amplitudes into a single distance/depth measurement having a suitable format. In other example embodiments, where the sensor system 112 includes a ToF sensor, a sensor controller for the sensor detects the round-trip times and converts the round-trip times into distance/depth values having a suitable format. In embodiments where the sensor system 112 includes a single-depth-of-focus sensor, a sensor controller may generate a parameter indicative of sharpness of focus (e.g., the amount/intensity of reflected light) for each distance between the sensor and a syringe surface. The sensor controller and/or the depth analysis unit 120 may then convert the parameter to a distance/depth value based on the known height of the sensor for each measured parameter value.

In the case of a one-dimensional scan, the scan may be viewed as a "depth profile." A single depth profile may reflect a set of consecutive syringes 102 (if the scan is continuous between one syringe in the next, e.g., within a particular syringe tub), or only a single syringe 102 (if the scan is discretely performed on each syringe). Due to the proximal perspective of the sensor(s) of the sensor system 112, the smallest distances/depths will generally correspond to the syringe flanges, while larger distances/depths will generally correspond to the syringe plungers within the syringe barrels. The depth analysis unit 120 also receives time and/or location (e.g., x-y coordinate) information (e.g., from the sensor positioning mechanism 114), which allows the depth analysis unit 120 to determine which scan points (or scan lines, etc.) correspond to which syringes. Algorithms that may be employed by the depth analysis unit 120 to determine plunger depths are discussed in more detail below. The depth analysis unit 120 may also compare the determined plunger depths to specified/desired ranges. Moreover, the depth analysis unit 120, or other software running within or external to the automated inspection station 100, may cause the plunger depths (possibly with indications of whether each plunger depth is within the specified range) to be stored in a local or remote memory, and/or communicated to another computing system, etc.

In some embodiments, the automated inspection station 100 includes, or is communicatively coupled to, one or more additional components not shown in FIG. 1. For example, the automated inspection station 100 may include or be communicatively coupled to a display. The display may use any suitable display technology (e.g., LED, OLED, LCD, etc.) to present information, such as the plunger depths determined by the depth analysis unit 120, and/or a visual notice when a plunger depth is not within the specified range, etc.

Figure 2:
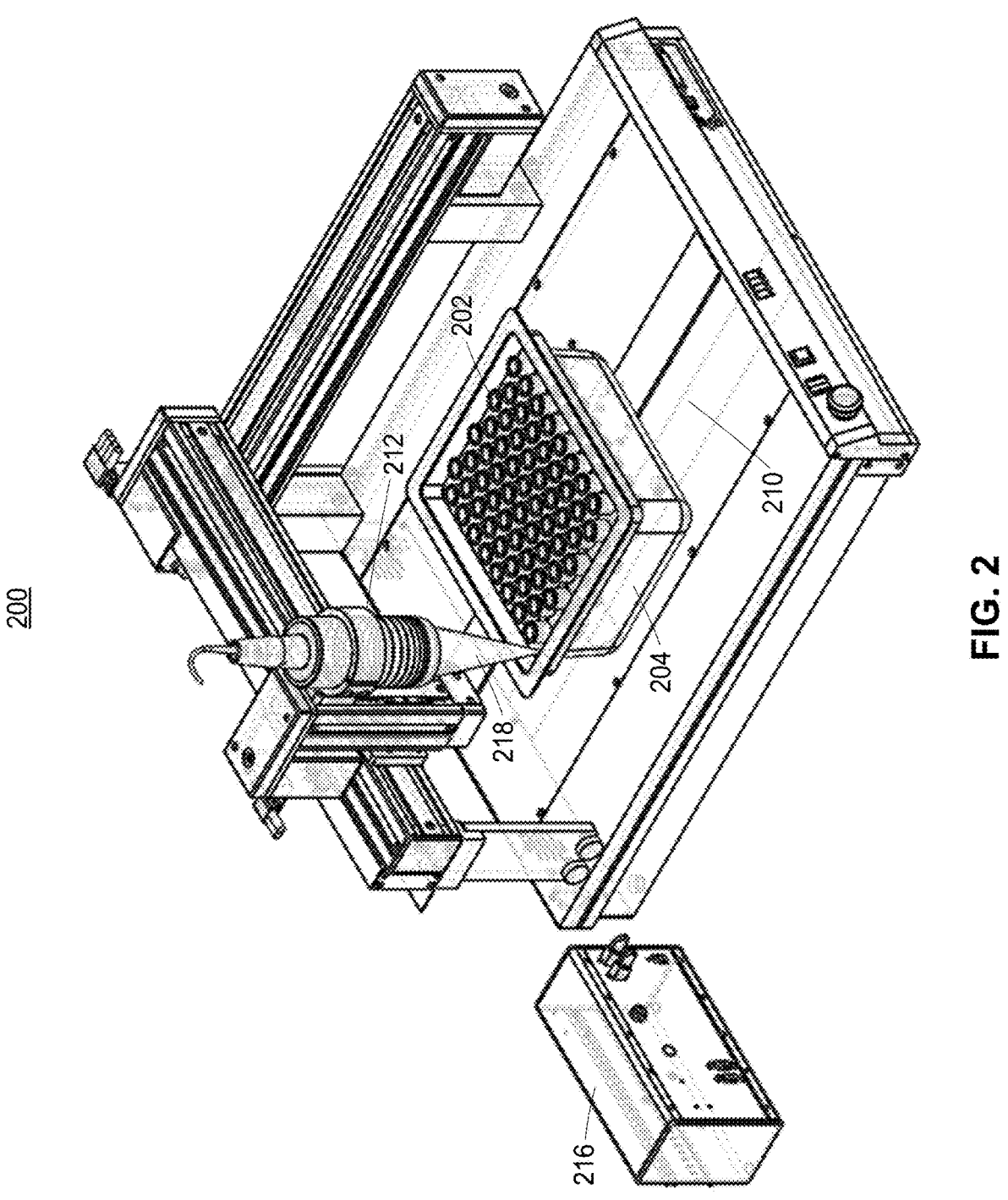
FIG. 2 is a perspective view of an example automated inspection station for inspecting syringes in tubs.

FIG. 2 is a perspective view of an example automated inspection station 200, which may be used as the automated inspection station 100 of FIG. 1 (or a portion thereof), for example. The embodiment of FIG. 2 reflects a stand-alone station, such as might be used in a laboratory (e.g., for qualification purposes), rather than line equipment that might include multiple automated inspection stations. In the example embodiment of FIG. 2, syringes 202 (e.g., the syringes 102) are held upright in a syringe tub 204, which is placed on a conveyor 210 (e.g., part of the syringe conveyance mechanism 110). The tub 204 may be configured to hold any suitable number of syringes 202 (e.g., 36, 49, 64, 81, 100, 160, etc.). Each of the syringes 202 may be "nested" in the tub 204 to prevent excessive movement.

The conveyor 210 moves so as to bring the syringe tub 204 to a position generally under a sensor 212 associated with a sensor controller 216 (e.g., collectively forming the sensor system 112), and then pauses its movement while the sensor 212 scans the syringes 202 in the syringe tub 204. FIG. 2 corresponds to an embodiment in which the sensor 212 is a confocal chromatic sensor or single-depth-of-focus sensor, the operation of which is represented in FIG. 2 by a light cone 218. In embodiments where the sensor 212 is a single-depth-of-focus sensor, the sensor 212 moves towards and/or away from a syringe 202 at each measurement point, in order to find the peak focus and thus the distance to a surface of the syringe 202. As noted above, however, a different type of sensor may be used instead, so long as the sensor 212 can detect distance/depth in a suitable range, and in a non-contact/non-destructive manner. The sensor 212 measurements are then processed by a depth analysis unit (e.g., the depth analysis unit 120), not shown in FIG. 2. The automated inspection station 200 may be used with an external computing device or system (e.g., a laptop or desktop computer) or integrated processing hardware acting as the depth analysis unit, for example.

FIG. 3 depicts one way in which plunger depth may be measured by the automated inspection station 100 or 200. It is understood, however, that any suitable definition or technique may be used (e.g., by the depth analysis unit 120) to calculate plunger depths. In FIG. 3, an example syringe 302 includes a plunger 330 disposed within a barrel 332. The proximal end of the barrel 332 (and of the syringe 302 as a whole) forms a flange 334, while a needle (obscured by a needle shield 336 in FIG. 3) is positioned at the distal end of the syringe 302. Typically, the barrel 332 and flange 334 are formed of glass, while the plunger 330 is formed of rubber. However, other materials may be used for either component (e.g., suitable types of plastic).

In the example embodiment shown, plunger depth for the syringe 302 is defined as the distance between (1) the proximal (or "top") surface 340 of the flange 334 and (2) the proximal/top surface 342 of the plunger 330. However, determination of these surfaces may be complicated by several factors. For example, the proximal flange surface 340 and/or proximal plunger surface 342 may be uneven (e.g., undulating with distinct peaks and troughs), in which case the depth analysis unit 120 may determine the distance to the proximal flange surface 340 and/or the distance to the proximal plunger surface 342 by averaging the scan points that correspond to the flange 340 and plunger 342, respectively, or by taking the peak values (smallest distance/depth) of those scan points, etc. The depth analysis unit 120 may also ignore certain features of the flange 334 and/or plunger 330 when determining the distances to the surfaces 340 and/or 342. For example, as shown in FIG. 3, the plunger 330 may have small "lugs" or "dimples" 344 protruding from its proximal surface 342, in which case the depth analysis unit 120 may determine the distance to the proximal plunger surface 342 by ignoring the dimples 344 (e.g., discarding the measurements/samples corresponding to the dimples 344 prior to averaging). As another example, the depth analysis unit 120 may determine the distance to the proximal flange surface 340 by ignoring any beveled edges of the flange 334 (e.g., discarding the measurements/ samples corresponding to the beveled edges prior to averaging).

The depth analysis unit 120 may also take other factors into account when determining distances/depths, such as the orientation of each syringe within its holder (e.g., star wheel, tub, Rondo tray, etc.). For example, syringes in a tray or tub are typically suspended from their flange, which may not be perfectly orthogonal to the cylindrical body (barrel) of the syringe. This can result in a slight tilt or squint, such as is depicted in FIG. 4 for a syringe 402 (with angular displacement 430). The plunger, too, may sit slightly squint in the syringe barrel. In some embodiments, the depth analysis unit 120 accounts for flange and/or plunger angular displacements by identifying the angle of the flange and/or plunger and, when that angle exceeds some threshold value, determining plunger depth using a different algorithm. For example, the depth analysis unit 120 may, in such instances, determine the flange surface depth based on the highest point of the proximal flange surface, and determine the plunger surface depth based on the highest point of the proximal plunger surface (possibly after discarding/ignoring measurements associated with dimples). Alternatively, the depth analysis unit 120 may always use the highest scan points for the flange and/or plunger, without checking whether there is an angular displacement. In still other embodiments, the depth analysis unit 120 performs a mathematical transform on the depth profile to remove or lessen any angular displacement prior to determining the proximal flange/plunger surfaces and calculating the plunger depth. Other techniques/algorithms are also possible.

The fill stage is by necessity a clean process with a relatively low risk of dust and debris, and the packaging environment (where plunger depth may be re-measured just before assembly of a combination device) is typically also relatively clean. However, some minimal level of dust/ debris contamination is unavoidable. In some embodiments, however, the sensor system 112 is by its nature resistant to dust, debris, and other small perturbations. In particular, confocal chromatic sensors and single-depth-of-focus sensors are generally insensitive to such perturbations, and the presence of dust/debris will generally have only a trivial effect on the sensor measurements.

Figure 5A:
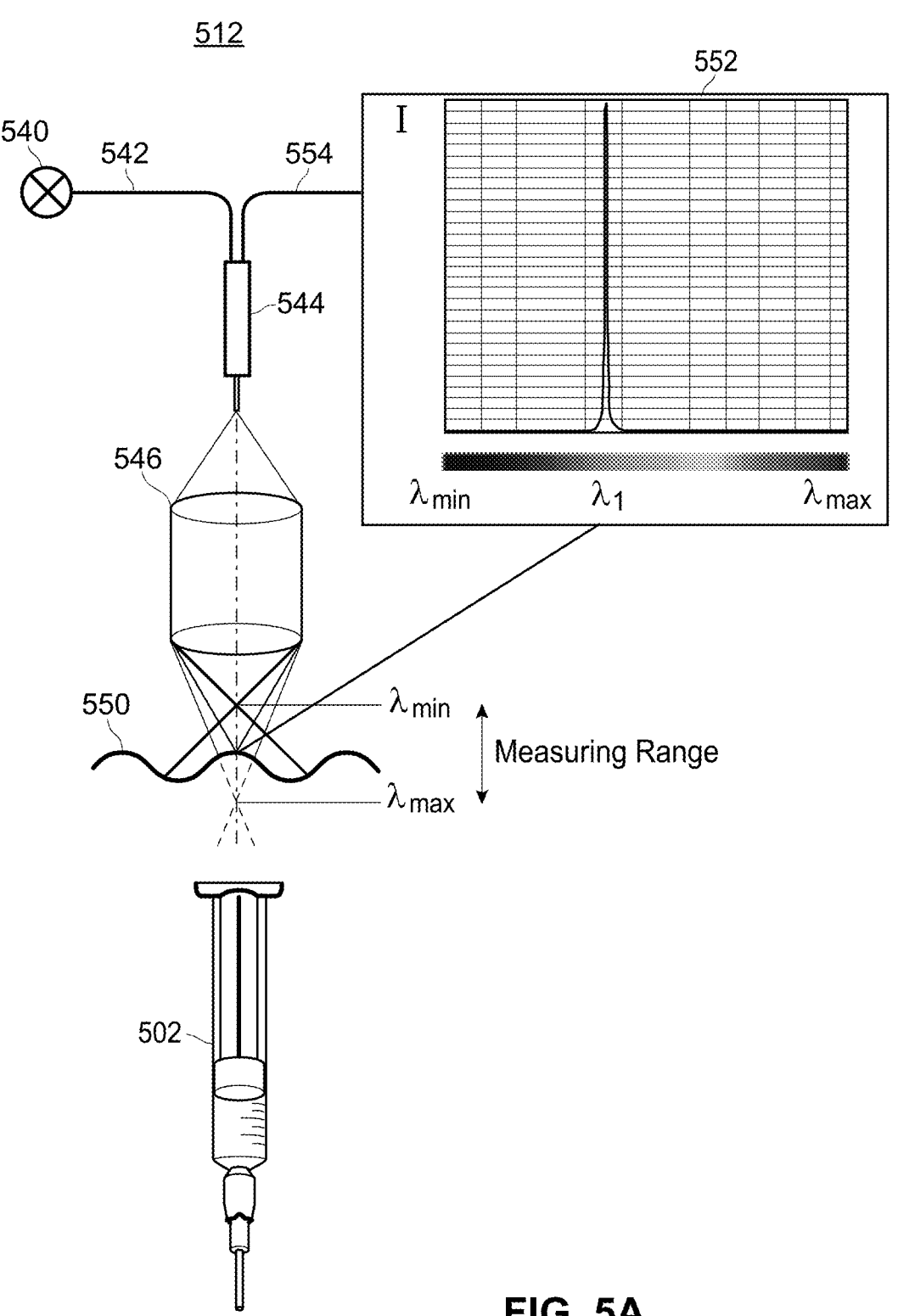
FIG. 5A depicts an example confocal chromatic sensor that may be used as the sensor of the automated inspection station of FIG. 1.

FIG. 5A depicts an example confocal chromatic sensor 512 that may be used in the sensor system 112 of the automated inspection station 100 of FIG. 1, or in another suitable automated inspection station. As seen in FIG. 5A, the confocal chromatic sensor 512 is placed above a given syringe 502, such that the confocal chromatic sensor 512 "looks down" into the proximal end of the syringe 502. A light source 540, which may be separate from the sensor head in order to maintain a purely passive sensor head that does not generate heat, generates white light. The white light propagates through a fiber optic cable 542 to a fiber coupler 544, and then through a set of vertically aligned passive lenses 546 (e.g., six or seven lenses).

The lenses 546 break the white light into its constituent frequency bands (i.e., different wavelengths/colors), and focus the light of the different frequencies at different distances from the sensor 512 (i.e., from the sensor head that includes the lenses 546). Specifically, the lenses 546 focus a shortest wavelength ($\lambda_{min}$) of the light the shortest distance from the sensor 512, and focus a longest wavelength ($\lambda_{max}$) of the light the longest distance from the sensor 512. The amount of light reflected by a surface for a particular wavelength/frequency is a function of how well-focused light of that frequency is at the point where the light impinges upon the surface. Stated differently, when a surface 550 is present at a particular distance within the measuring range, the intensity of the reflected light is greatest for the specific wavelength ($\lambda_1$) of light that is best focused at the distance of that surface 550. Thus, for any given measurement/scan point, the amount/intensity of the reflected light at each wavelength is indicative of the depth/distance (relative to the sensor 512) at that measurement/scan point. This phenomenon is illustrated by the example plot 552 in FIG. 5A. The reflected light passes through the lenses 546, fiber coupler 544, and another fiber optic cable 554 before being analyzed by the depth analysis unit 120. As noted above, testing shows the use of a confocal chromatic sensor to be particularly well-suited to depth detection for glass syringes having rubber plungers. Moreover, a confocal chromatic sensor can provide measurements at a very high sampling rate (e.g., about 70,000 samples per second), thereby providing high throughput relative to other, conventional techniques.

Figure 6A:
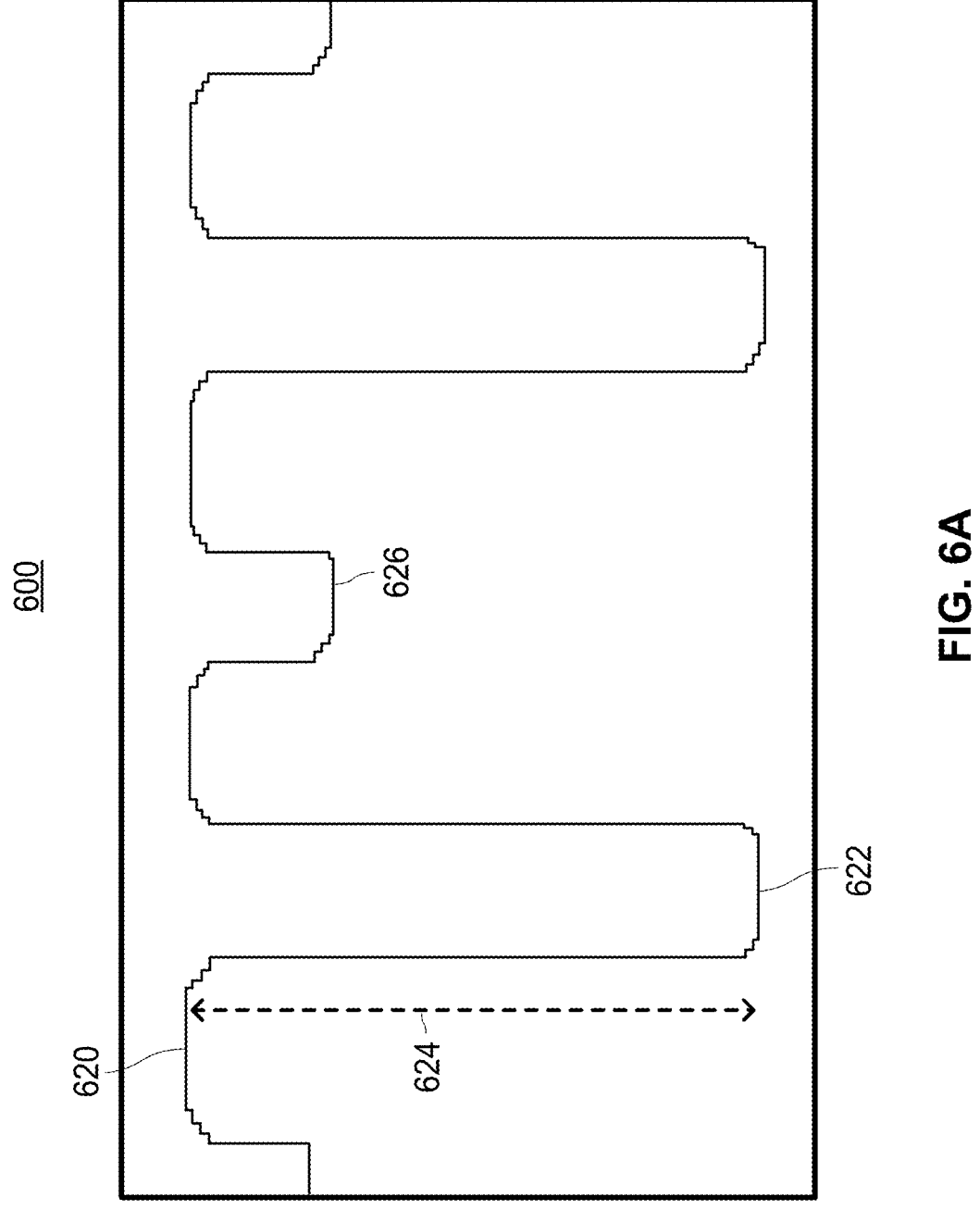
FIGS. 6A and 6B depict an example depth profile and depth image, respectively, that may be generated using the sensor system of FIG. 1.
Figure 6B:
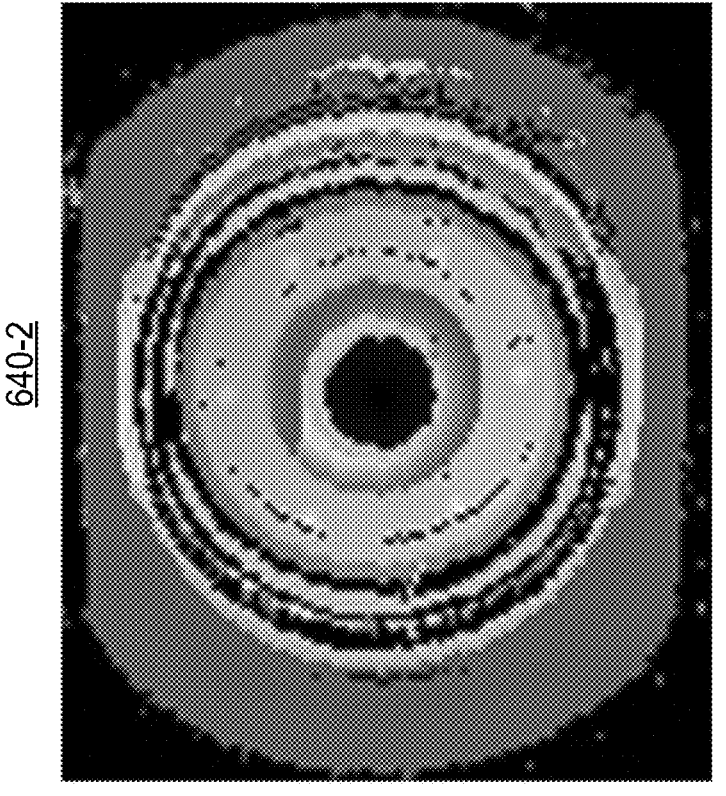
Figure 6B:
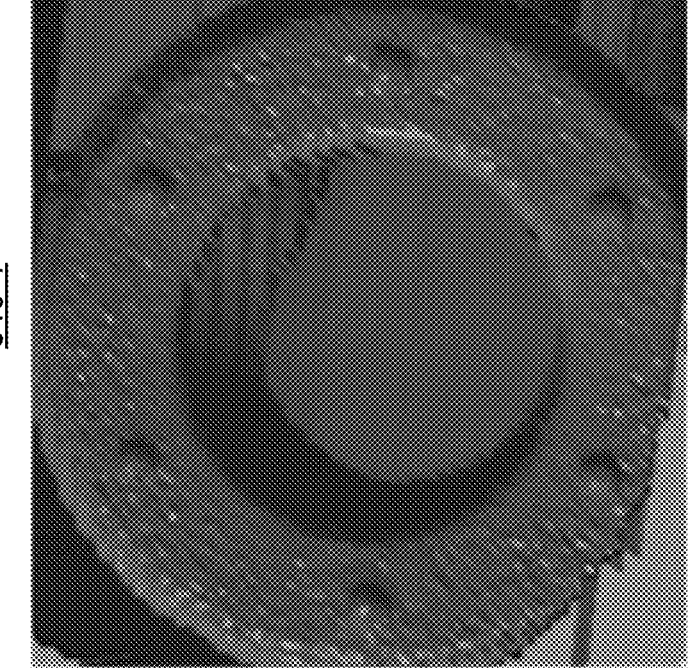

The sensor controller (and/or depth analysis unit 112) then converts the intensity versus wavelength (or intensity versus frequency, etc.) information for each point of the scan to a distance/depth, thereby generating a one-dimensional "depth profile" or two-dimensional "depth image" (depending on the scan pattern). An example depth profile and depth image are shown in FIGS. 6A and 6B, respectively. Referring first to FIG. 6A, a depth profile 600 represents a continuous scan by a sensor of the sensor system 112 (e.g., by the sensor 512) across two 1 mL glass syringes that are positioned next to each other (e.g., within a tub, Rondo tray, star wheel, etc.). The scan may be a straight-line pass over the syringes, or a slightly arced line (e.g., if the syringes are held in a rotating star wheel), for example. In some alternative embodiments, one or more mirrors reside in the optical path between the sensor 512 and the syringe 502, such that the sensor 512 need not "look" directly into the proximal end of syringe 502. In the depth profile 600, depth 620 corresponds to the proximal surface of a syringe flange, depth 622 corresponds to the proximal surface of a syringe plunger, and depth 626 corresponds to an area between successive syringes. The depth analysis unit 120 calculates the plunger depth 624 as the difference between the depth of the surface 620 and the depth of the surface 622. As noted above, the depth analysis unit 120 may apply various filtering or other processing techniques before calculating the plunger depth 624, such as averaging the points across each surface 620 or 622, ignoring beveled edges and/or dimples, and so on. The depth analysis unit 120 may determine which plunger depth corresponds to which syringe based on time (e.g., time stamp) and/or location (e.g., x-y coordinate) information output by the sensor positioning mechanism 114, for example. While the description herein primarily relates to scan "points," it is understood that, in some embodiments, a sensor head (e.g., a confocal chromatic sensor head) can move in order to measure a scan line.

Figure 5B:
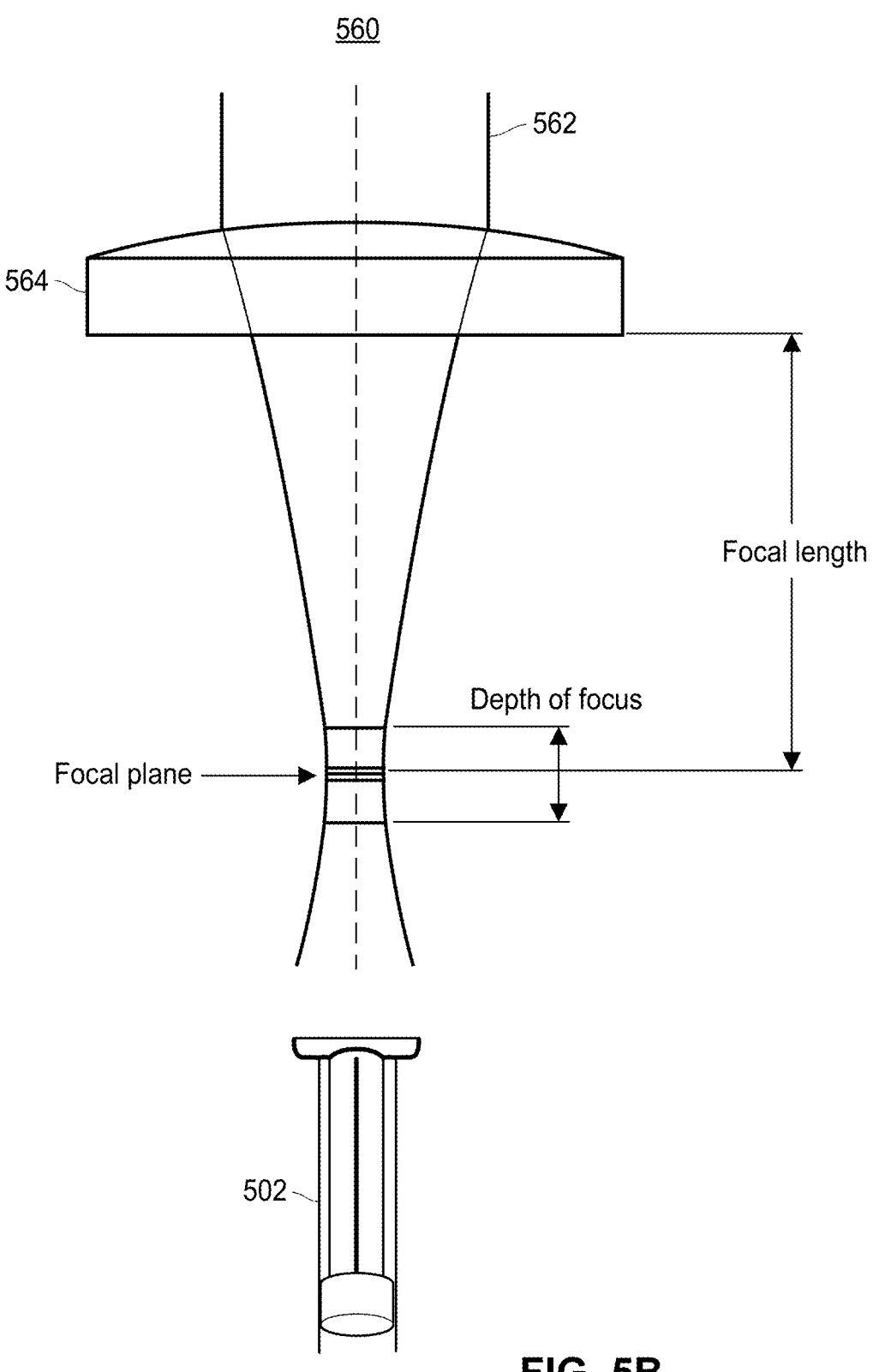
FIGS. 5B and 5C depict an example single-depth-of-focus sensor that may be used as the sensor of the automated inspection station of FIG. 1.
Figure 5C:
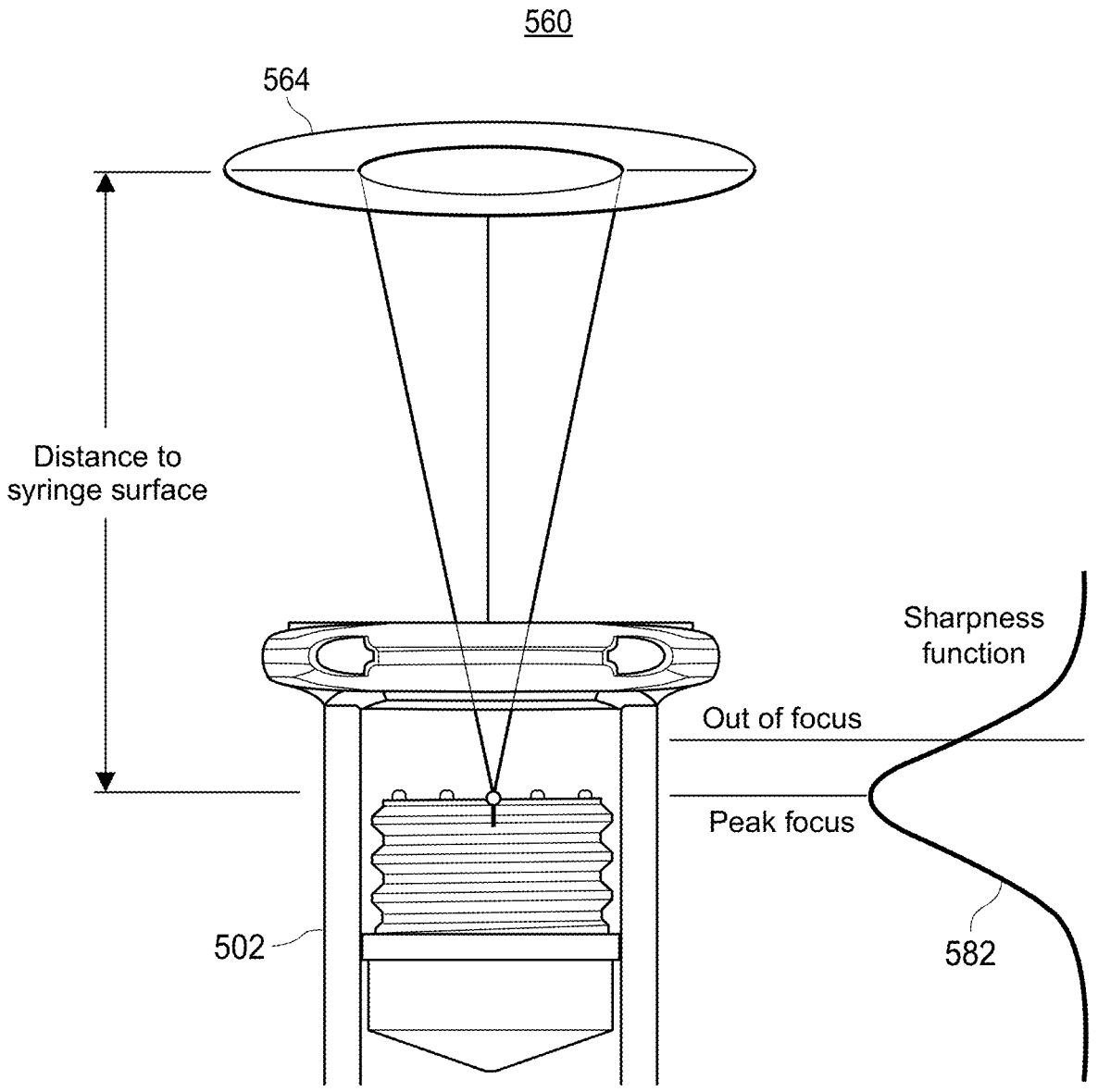

FIGS. 5B and 5C depict an example of an alternative, single-depth-of-focus sensor 560 that may be used in the sensor system 112 of the automated inspection station 100 of FIG. 1, or in another suitable automated inspection station. As seen in FIG. 5B, the single-depth-of-focus sensor 560 is placed facing (e.g., above) the proximal end of a given syringe 502, such that the single-depth-of-focus sensor 560 "looks down" into the proximal end of the syringe 502. Light 562 from a light source, which may be separate from the sensor head in order to maintain a purely passive sensor head that does not generate heat, may be monochromatic (e.g., a single wavelength), for example. The light 562 propagates through a lens 564. As seen in FIG. 5B, the lens 564 is associated with a single, fixed focal length, focal plane, and depth of focus. Preferably, the lens 564 has a small/narrow depth of focus (e.g., 1 millimeter or less). While not shown in FIG. 5B or FIG. 5C, the sensor 560 includes a camera to measure the level of focus at each distance from the syringe surface (e.g., by measuring the amount/intensity of reflected light).

As the distance between the lens 564 and the syringe surface changes, the syringe surface can come further into focus or go further out of focus. FIG. 5C shows a sharpness function 582 that is indicative of focus, the values of which may be generated by the sensor controller. A peak value of the sharpness function 582 corresponds to the focal plane shown in FIG. 5B. Notably, measurement accuracy and precision are not necessarily limited to the depth of focus of the lends 564. For example, the sensor controller may calculate the position of the focal plane by determining distances where the level of focus starts to fall, or falls below some threshold value relative to the peak detected value, etc. In this way, the distance to the syringe surface can be measured with finer granularity than the depth of focus. For example, a lens 564 with a 1 millimeter depth of focus can potentially offer a measurement precision/granularity of 5 micrometers or less. As with the sensor 512 of FIG. 5A, the optical path between the sensor 560 and the syringe 502 may or may not be redirected by one or more mirrors.

The single-depth-of-focus sensor 560 has certain advantages and disadvantages relative to the confocal chromatic sensor 512 of FIG. 5A. The confocal chromatic sensor 512 can potentially use simpler mechanisms to move the sensor 512 relative to the syringes, because no movement of the sensor 512 is needed towards and/or away from each syringe (e.g., in the Z-direction). Moreover, because there is no need to move the confocal chromatic sensor 512 towards or away from each syringe, the sensor 512 can capture each measurement point more quickly than the single-depth-of-focus sensor 560. Nonetheless, the single-depth-of-focus sensor 560 can potentially enable faster scanning than the confocal chromatic sensor 512. In particular, due to both the lower cost and the smaller diameter needed for the camera and lens 564, the single-depth-of-focus sensor 560 provides the potential to use far more sensors (e.g., 160 small, low-cost cameras/lenses for a 160-syringe tub) than would be feasible with confocal chromatic sensors. By using numerous single-depth-of-focus sensors 560 (cameras/lenses) in parallel, multiple syringes (e.g., a full tub of syringes) can be measured almost instantly, in some embodiments.

In some embodiments, and regardless of sensor type (e.g., the sensor 512 or the sensor 560), a depth profile such as the depth profile 600 is produced by running a single sensor of the sensor system 112 over the center of each syringe 102. Running the sensor over each syringe 102 only once results in high throughput, but at the cost of lower precision. In particular, precision may suffer because the single pass of the sensor may fail to capture the highest point of the flange and/or plunger, and/or fail to account for any squint angle of the syringe and/or plunger. In scenarios where lower fidelity measurements are acceptable, however, this may be an acceptable trade-off in order to achieve higher throughput.

In other embodiments, precision is increased by running a single sensor of the sensor system 112 multiple times over a single syringe 102 (e.g., three times, or five times, etc.), with each successive pass being at a slight offset in one axis relative to the previous pass. Increasing the number of passes increases the likelihood that any subtleties in the shape or alignment of the flange and/or plunger will be captured, at the cost of reduced throughput.

In still other embodiments, precision is further increased by more rigorously scanning each syringe in two-dimensions (e.g., in a raster pattern), such that the number of scan lines and the resolving power of the sensor 112 result in a complete, or nearly complete, "depth image" of the flange and/or plunger. FIG. 6B depicts a depth image 640 created in this manner (shown here as two distinct depth image portions 640-1 and 640-2), after the software has collated and interpreted the individual one-dimensional raster lines). By combining the depth information from the depth image portions 640-1 and 640-2, the depth analysis unit 120 can accurately calculate the plunger depth. In other embodiments, only a single depth image is generated for each syringe 102, with no need to combine separate plunger and flange depth images.

In the depth image portion 640-1, the proximal plunger surface appears as a ring with dimples/lugs around the circumference of the proximal plunger surface (which the depth analysis unit 120 may ignore when calculating plunger depth). In the depth image portion 640-2, the outermost, generally concentric portion represents the proximal flange surface. Cartesian robots are particularly well suited to quickly running a sensor over the same syringe multiple times in order to generate a two-dimensional scan, and the raster pattern (or snake pattern, etc.) is particularly well suited to minimizing the time for such a scan. The depth analysis unit 120 can combine one-dimensional scan lines to form a two-dimensional depth image.

Due to the relatively simple data processing needed when using a depth profile (as opposed to the processing needed for conventional machine vision techniques), the sensor motion (through the scan pattern) may limit throughput more than data processing time. The time required to move the sensor for a full two-dimensional scan may be long enough to make the approach more suitable for offline measurements than for integration into the production line. In some embodiments, however, two-dimensional scanning speed is increased by using multiple sensors (e.g., two, three, or more confocal chromatic or single-depth-of-focus sensors) that are positioned with slight lateral offsets in one axis relative to each other. As sensor technology improves and sensor size is reduced (for a given depth of field), more scan lines can be generated in parallel, further increasing the two-dimensional scan speed.

Figure 7:
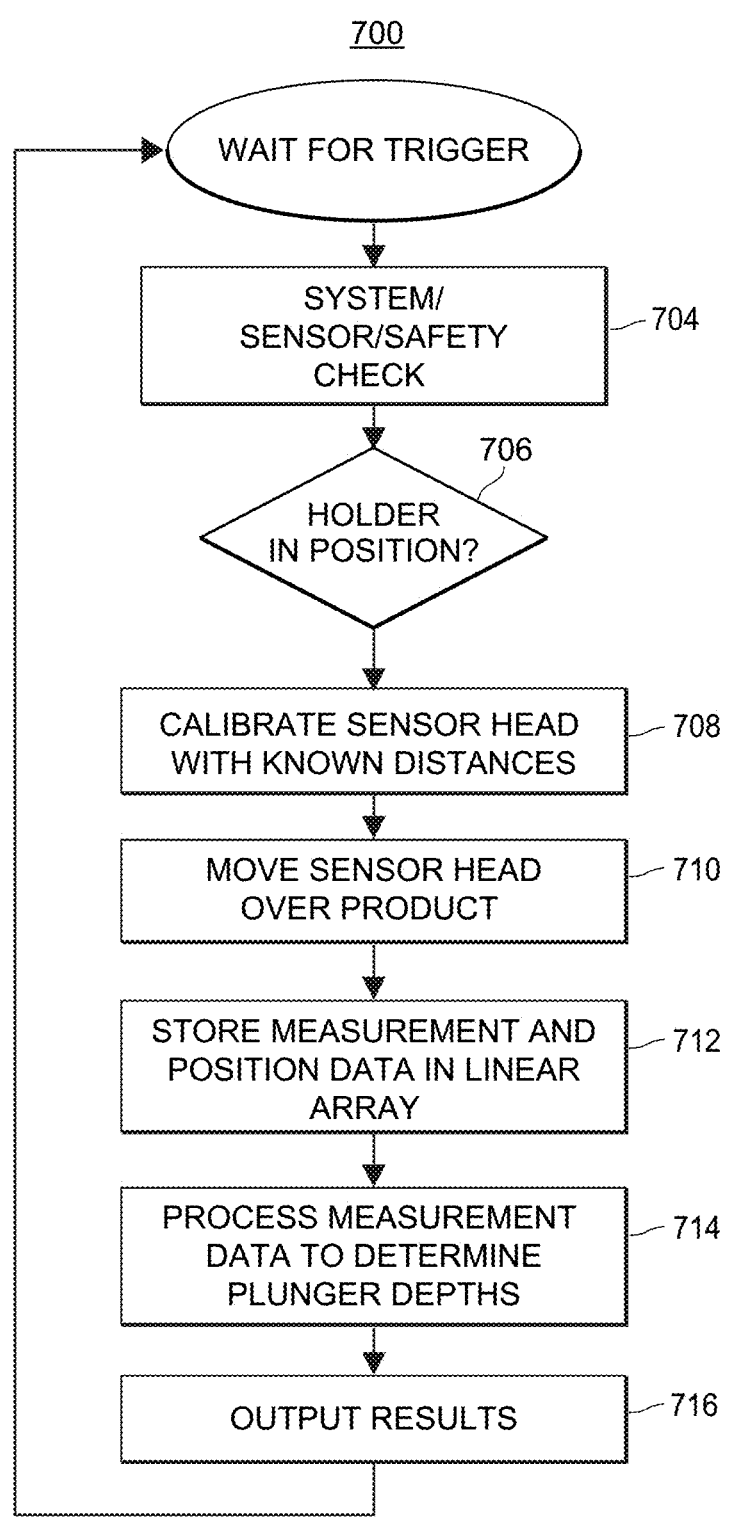
FIG. 7 is a flow diagram of an example algorithm that may be implemented by the automated inspection station of FIG. 1.

FIG. 7 is a flow diagram of an example algorithm 700 that may be implemented by the automated inspection station 100 of FIG. 1. The algorithm 700 may be implemented in whole or in part by the sensor system 112, the sensor positioning mechanism 114, and the depth analysis unit 120, for example. For ease of explanation, however, algorithm 700 is described below with general reference to actions being taken by "the system." While the algorithm 700 is described with respect to an embodiment in which a sensor (e.g., a sensor of the sensor system 112) performs a one-dimensional scan, the same principles can apply for two-dimensional scans.

In the example algorithm 700, at stage 702, the system waits for a trigger, such as the manual pressing of a button, or the arrival of a syringe or syringe holder (e.g., syringe tub). At stage 704, after detecting the trigger, the system performs various checks. For example, the system may check for proper operation of various hardware and/or software components, including the sensor system 112, and perform a safety check.

At stage 706, the system determines whether a holder for one or more syringes is in position for scanning. For example, the system may determine whether a syringe tub has been advanced (e.g., by the syringe conveyance mechanism 110) to the appropriate scanning location. Stage 706 may be accomplished using a relatively quick, preliminary scan of the tub (e.g., a location check for tub edges), for example. At stage 708, the system calibrates the sensor head at one or more locations having known distances from the sensor head. For example, the sensor positioning mechanism 114 may move the sensor(s) of the sensor system 112 to a location that is near the syringes 102 and has a known distance from the sensor(s) of the sensor system 112. A scan controller of the sensor system 112 can then determine any appropriate calibration factors (e.g., distance offsets) to be applied when determining the depth/distance at each scan/measurement point.

In some embodiments, the system also performs a preliminary scan (e.g., with higher-speed sensor movement and lower density of scan points) to determine which portions of the tub are populated with syringes. In such an embodiment, the successive stages (e.g., stage 710) may be restricted to only those general locations in which a syringe is present, thereby improving efficiency/throughput.

At stage 710, the system moves the sensor head over the product (e.g., a single syringe, or syringes in a tub, etc.) in the desired scan pattern. In some embodiments, stage 710 includes moving the sensor head over each syringe at a constant velocity, accelerating when reaching an area with no syringe, and then decelerating back to the constant velocity when reaching the next syringe (e.g., based on known syringe positions, or based on syringe positions as determined from a preliminary scan, etc.). As the sensor head moves and captures depth information, the system at stage 712 stores the measurements, as well as position data (e.g., encoder outputs from the sensor positioning mechanism 114), in a linear array in a memory. At stage 714, the system processes the stored measurement data, along with the position data, to determine plunger depths for each of the syringes covered by the scan. Stage 714 may occur after the full scan at stages 710 and 712, or in parallel with the full scan. Stage 714 may include applying calibration factors, checking for any angular displacements, and so on.

At stage 716, the system outputs the results (e.g., the determined plunger depths with indicators of the corresponding syringes). Stage 716 may include presenting the results on a display, storing the results to a file, communicating the results to another computing system, and/or other operations.

FIGS. 8-12 depict various types of automated inspection stations that may be used, for example, as the automated inspection station 100 of FIG. 1, depending on the manner in which syringes are conveyed.

Figure 8:
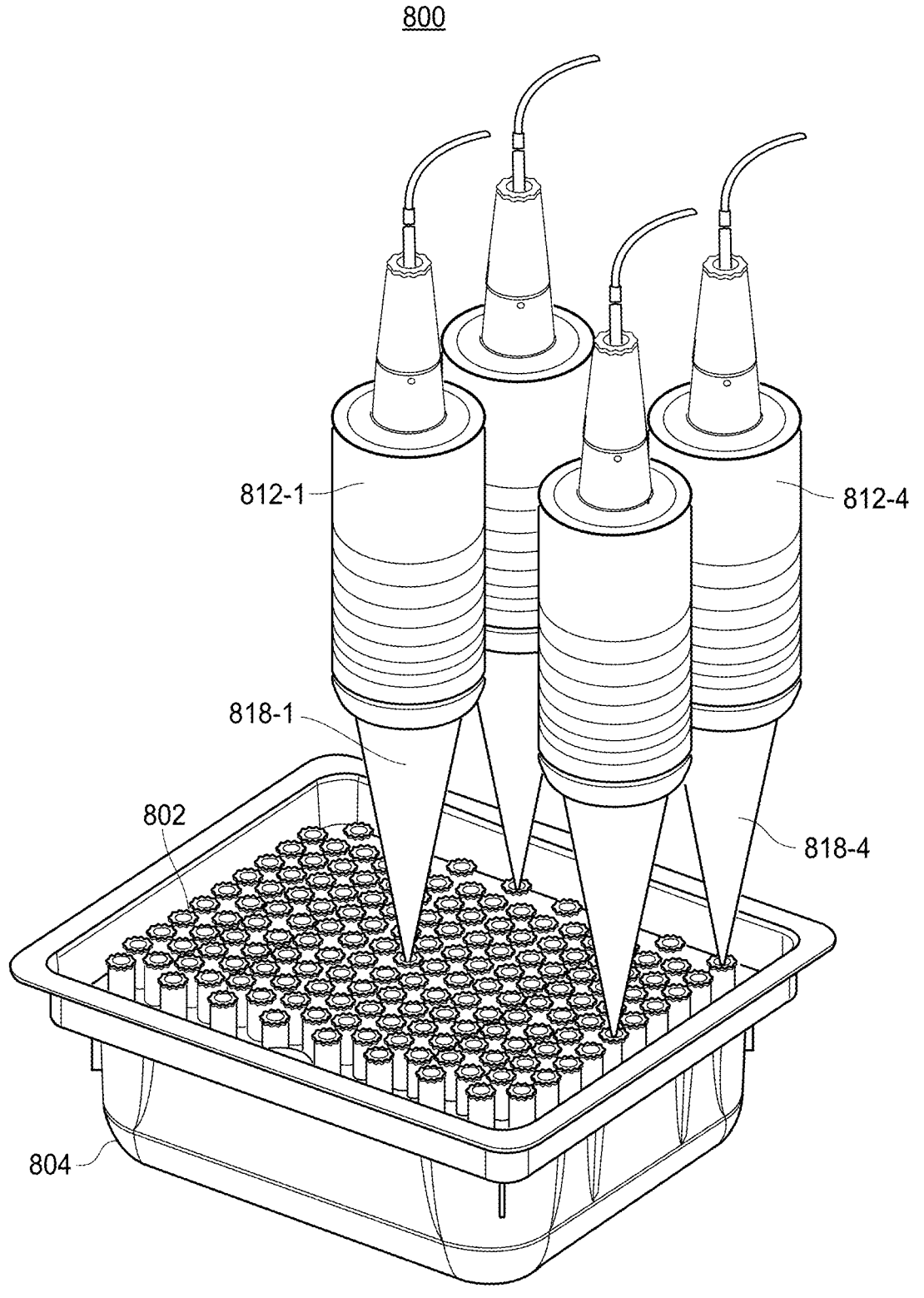
FIG. 8 is a perspective view of an example automated inspection station for inspecting syringes in tubs using multiple sensors.

Referring first to FIG. 8. an example automated inspection station 800 for inspecting syringes 802 in a tub 804 uses multiple sensors 812-1 through 812-4 (unlike the single sensor embodiment shown in FIG. 2). While FIG. 8 shows an example in which each sensor 812 is a confocal chromatic sensor with a corresponding light cone 818, the sensors 812 may be any type of sensor discussed herein (e.g., a single-depth-of-focus sensor, a ToF sensor, etc.). In other embodiments, the automated inspection station 800 may include more or fewer than four sensors 812.

The tub 804 may be similar to the tub 204 of FIG. 2, and each syringe 802 may be similar to a syringe 202 of FIG. 2 and "nested" within the tub 804 to prevent excessive movement. While not shown in FIG. 8, the tub 804 may be moved via a conveyor similar to the conveyor 210. The conveyor moves so as to bring the syringe tub 804 to a position generally under the sensors 812-1 through 812-4, and then pauses its movement while each of the sensors 812-1 through 812-4 scans a different one of the syringes 202 in the syringe tub 804. The sensor 812 measurements are then processed by a depth analysis unit (e.g., the depth analysis unit 120), not shown in FIG. 8. The automated inspection station 800 may be used with an external computing device or system (e.g., a laptop or desktop computer) or integrated processing hardware acting as the depth analysis unit, for example.

The automated inspection station 800 can improve throughput by scanning different subsections of the tub 804 in parallel. In the depicted example, the set of sensors 812-1 through 812-4 are moved in unison (e.g., by sensor positioning mechanism 114) to sequentially pause above each syringe in the respective quadrants. While positioned/paused above a given set of four respective syringes 802, the sensors 812-1 through 812-4 are moved more in smaller increments (again in unison, e.g., by sensor positioning mechanism 114), to scan the surface(s) of the four syringes 802. For coordinated/synchronized movement, the sensors 812-1 through 812-4 may be mounted together on a common, two-axis horizontal actuator.

Preferably, the shape of the tub 804 and the number of syringes 802 in the tub 804 corresponds to the number of sensors 812. In the embodiment shown, for example, it may be desirable to use a tub 804 that holds a 2N×2N array of syringes 802, where N is any integer greater than zero (but likely with a larger minimum N, assuming that sensor size constrains how closely the sensors 812 can be positioned relative to one another), and with a spacing of N syringes 802 between each sensor 812. Each syringe 802 in the tub 804 is scanned by only a single sensor 812 (unless some level of redundancy is desired), with throughput increasing as the number of sensors 812 increases (e.g., as technological improvements allow sensor size to decrease, thereby allowing more densely packed sensors 812). Mirror and/or other optics may also be used to increase the density of the sensors 812, and thus increase throughput. The general principals underlying the automated inspection station 800 may be extended to any size array of sensors 812 and syringes 802. For example, a 3×2 array of sensors 812, with a spacing of eight syringes 802, may be used to efficiently scan a 24×16 array of syringes 802.

Figure 9A:
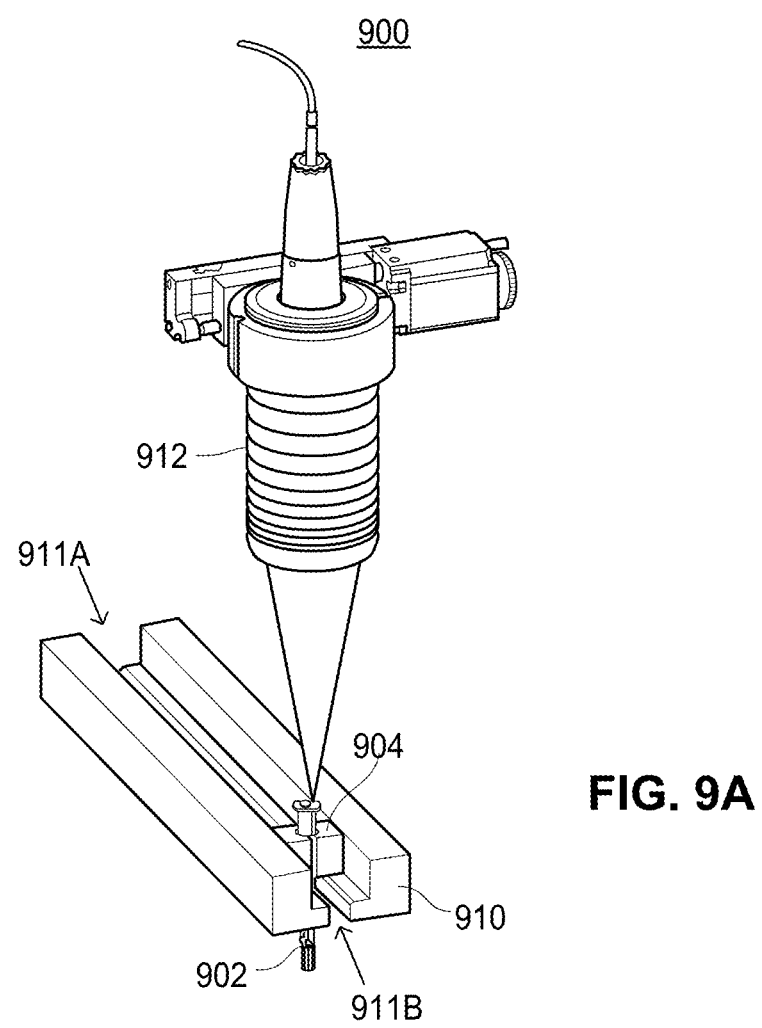
FIGS. 9A-9D are various perspective and overhead views of an example automated inspection station for inspecting syringes in a linear conveyance mechanism.

FIGS. 9A-9D are various perspective and overhead views of an example automated inspection station 900 for inspecting syringes in a linear conveyance mechanism 910. As seen in FIG. 9A, the linear conveyance mechanism 910 provides a straight, recessed channel 911A in and along which a chuck 904 can move (e.g., in response to a drive motor or pneumatic system not shown in FIG. 9A). The chuck 904 is configured to hold a single syringe 902, with a portion of the syringe barrel extending through a gap 911B in the channel 911A. The chuck 904 may be a friction chuck, in order to ensure that the syringe 902 does not rotate between scans/measurements. A high fidelity, linear conveyor may move the chuck 904 (and thus, the syringe 902) in small, precise increments along the channel 911A. For each increment in which the chuck 904 is below the sensor 912 (e.g., a confocal chromatic sensor or any other sensor type discussed herein), a linear motor scans the sensor 912 laterally across the proximal end (flange) of the syringe 902 (e.g., with micron-level precision), while the chuck 904 and syringe 902 remain in a fixed/static position. Each such scan produces a one-dimensional depth profile (e.g., similar to a portion of depth profile 600). By varying the increment size, the measurement density and corresponding throughout can be controlled. For example, a 1 mm increment size may be small enough to produce a reasonably good two-dimensional depth map for production purposes. The sensor 912 measurements are then processed by a depth analysis unit (e.g., the depth analysis unit 120), not shown in FIG. 9. The automated inspection station 900 may be used with an external computing device or system (e.g., a laptop or desktop computer) or integrated processing hardware acting as the depth analysis unit, for example.

Figure 9B:
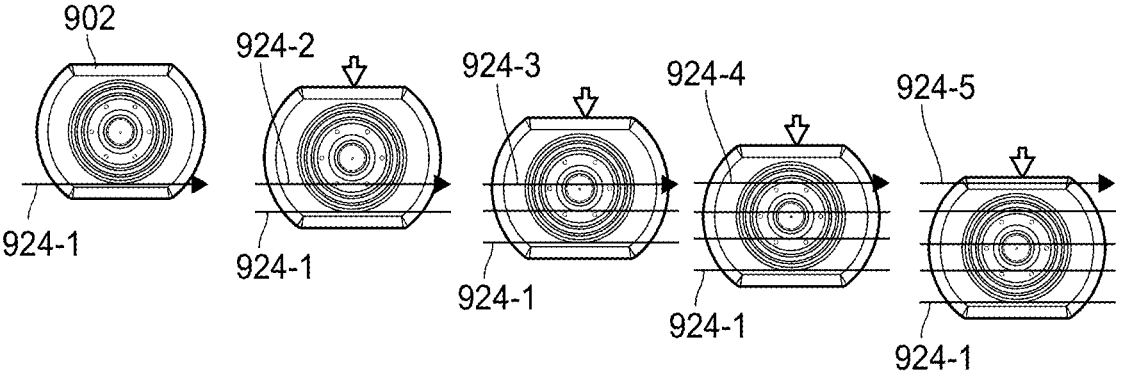

FIG. 9B provides an overhead view of the scan paths 924-1 through 924-5 across a syringe 902 when using the automated inspection station 900. At each position of the syringe 902, as the syringe 902 and chuck 904 move along the channel 911A, the sensor 912 performs a new linear scan, depicted in FIG. 9B as the top-most line/arrow at each successive increment. Each syringe position shown in FIG. 9B corresponds to a different time/increment, starting at the left of FIG. 9B and proceeding to the right of FIG. 9B. In other embodiments and/or scenarios, the increments may be larger (resulting in fewer than five scan paths 924) or smaller (resulting in more than five scan paths 924).

Figure 9C:
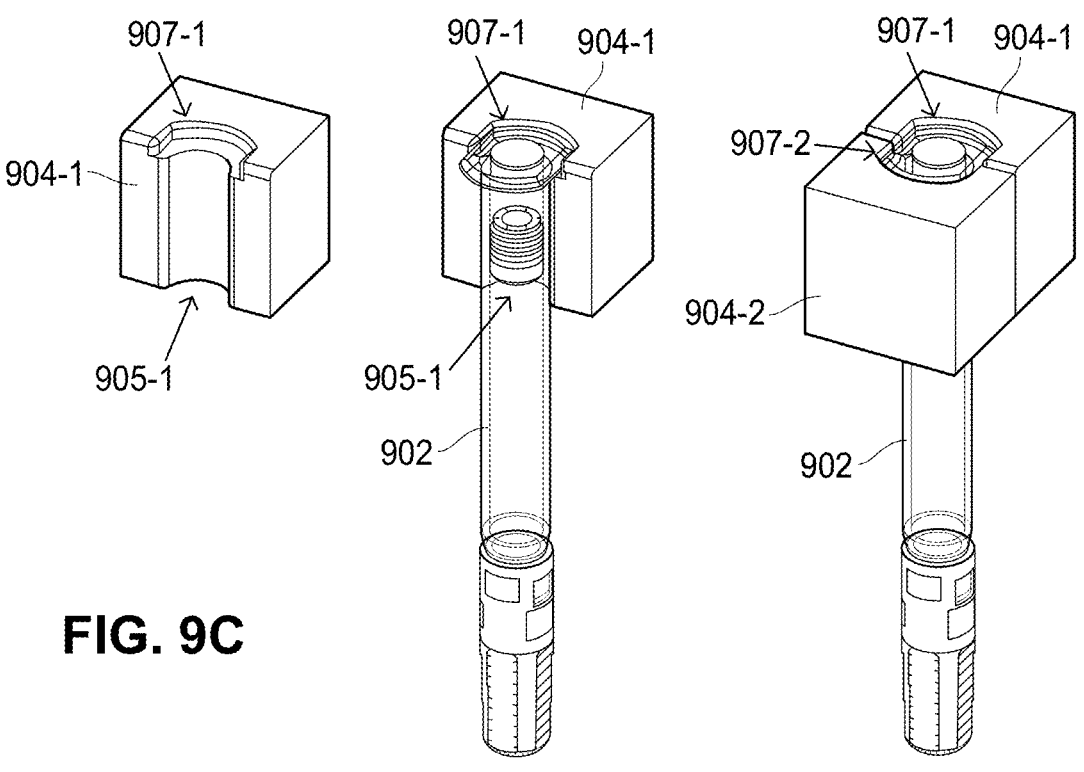
Figure 9D:
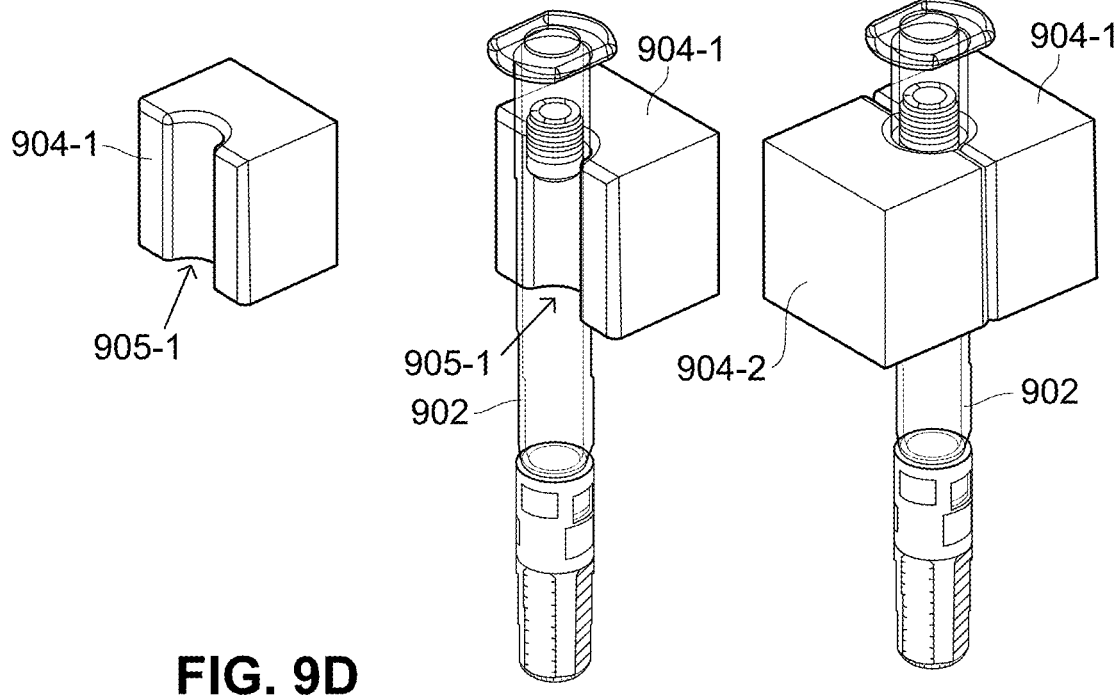

FIGS. 9C and 9D show two alternative designs that may be used for the chuck 904 of the automated inspection station 900. As seen in FIG. 9C, a first design of the chuck 904 includes two chuck halves 904-1 and 904-2 with respective halves 905-1 and 905-2 (the latter not shown in FIG. 9C) of an opening 905 and respective halves 907-1 and 907-2 of a recess 907. When the chuck halves 904-1 and 904-2 are joined around a syringe 902, the barrel of the syringe 902 protrudes through the opening 905, and the flange of the syringe nests securely in the recess 907. The recess 907 fits the flange precisely enough so as to prevent, or at least substantially reduce, rotation of the syringe 902 within the chuck 904. An advantage of this design is that no friction/adhesion is required to prevent syringe 902 rotation (although some embodiments may also use friction and/or adhesion). A potential disadvantage is a higher risk of breakage for glass of the syringe 902, due to interaction between the glass flange and chuck 904. The design may also be unsuitable if there are any significant differences in flange dimensions (e.g., due to syringe manufacturing tolerances). Furthermore, the design does not prevent rotation of syringes that have circular flanges.

An alternative design of the chuck 904 is shown in FIG. 9D. In this design, the chuck 904 again includes two chuck halves 904-1 and 904-2 with respective halves 905-1 and 905-2 (the latter not shown in FIG. 9D) of an opening 905, and again with the barrel of the syringe 902 protruding through the opening 905 when the two chuck halves 904-1 and 904-2 are joined around a syringe 902. However, this second design does not include the recess 907 to secure the rotational orientation of the syringe flange, and the flange remains entirely outside the chuck 904. To prevent or substantially reduce syringe rotation, the opening 905 has a high friction and/or adhesion surface to firmly hold each syringe 902. In some embodiments, the chuck 904 includes one or more suction cups on the surface of the opening 905, in order to temporarily fix a given syringe 902 in place and prevent rotation or other movement relative to the chuck 904. A benefit of this second design is that the risk of breakage is decreased due to the lack of contact with the flange. A potential disadvantage is that the high friction/adhesion surface material may wear out and become less effective over time and require replacement. Moreover, unless carefully designed, the surface material could potentially leave particulates/deposits on the barrel of the syringe 902.

Figures 10A, 10B, 10C, 10D:
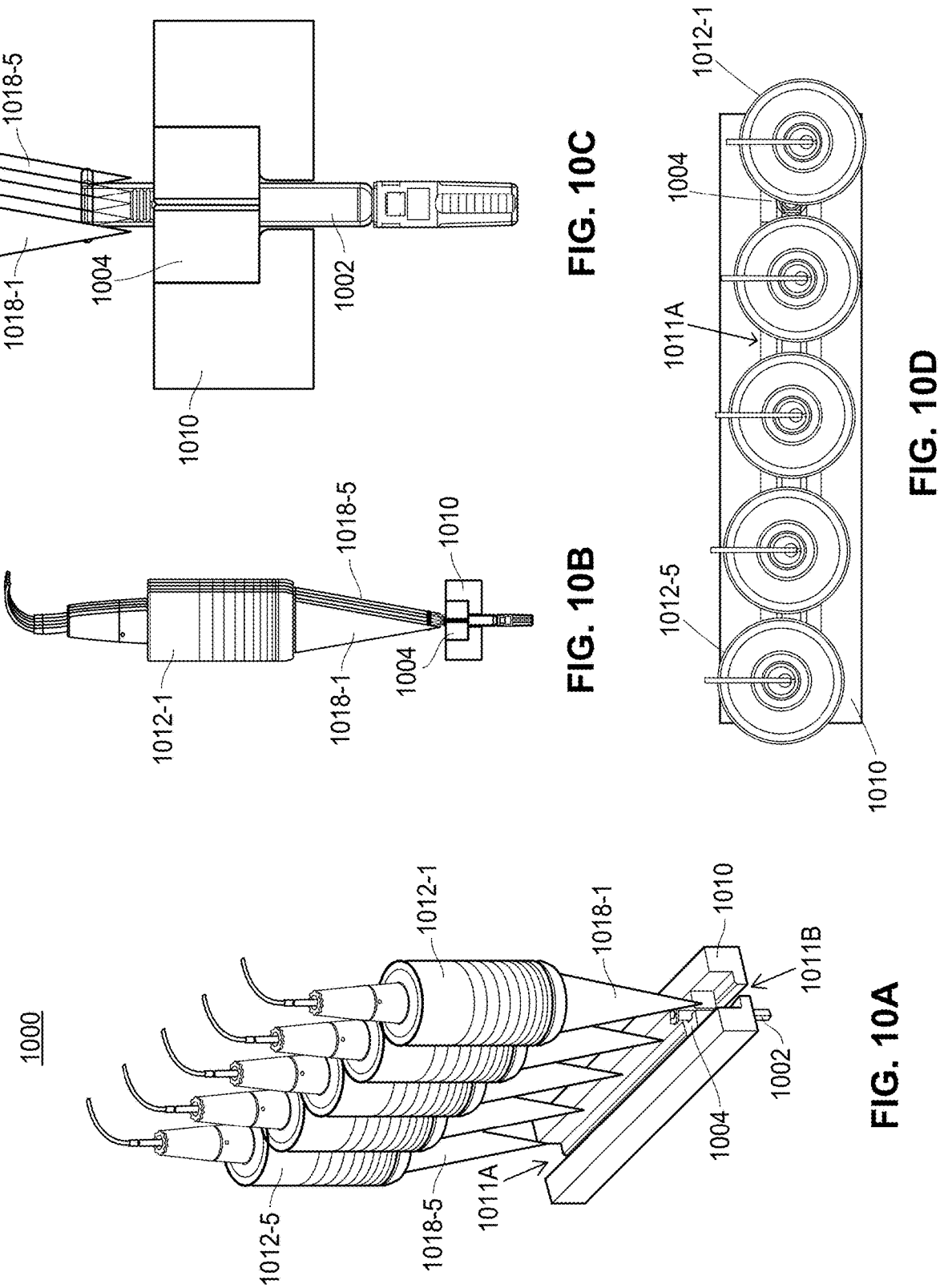
FIGS. 10A-10D are various perspective and overhead views of an example automated inspection station for inspecting syringes in a linear conveyance mechanism using multiple sensors.

FIGS. 10A-10D are various perspective and overhead views of another example automated inspection station 1000 for inspecting syringes 1002 in a linear conveyance mechanism 1010 using multiple sensors 1012. As seen in FIG. 10A, the linear conveyance mechanism 1010 provides a straight, recessed channel 1011A in and along which a chuck 1004 can move (e.g., in response to a drive motor or pneumatic system not shown in FIG. 10A). The chuck 1004 (e.g., similar to chuck 904) is configured to hold a single syringe 1002, with a portion of the syringe barrel extending through a gap 1011B in the channel 1011A. A linear conveyor may move the chuck 1004 (and thus, the syringe 1002) along the channel 1011A. Unlike the station 900 of FIG. 9, the linear conveyor may move the chuck 1004 and syringes 1002 continuously along the channel 1011A, rather than in discrete increments, and the sensors 1012 may all have fixed positions relative to the channel 1011A. To cover at least some extent of the width of the channel 1011A, the automated inspection station 1000 includes five sensors 1012-1 through 1012-5 that are arranged along the length of the channel 1011A and staggered laterally across the channel 1011A with small offsets relative to each other, as seen in FIGS. 10A-10D. The sensors 1012-1 through 1012-5 may be confocal chromatic sensors (as shown in FIG. 10A-10C, with light cones 1018-1 through 1018-5, respectively), or any other sensor type discussed herein. While five sensors 1012 are shown in FIG. 10, other embodiments may have more or fewer sensors.

The sensors 1012-1 through 1012-5 may operate one at a time (e.g., sequentially as the chuck 1004 and syringe 1002 pass beneath each sensor 1012), or in parallel (e.g., on different syringes 1002 held by different chucks 1004 at different positions along the channel 1011A). Due to the movement of the chuck 1004 and syringe 1002 along the channel 1011A, and the fixed sensor 1012 orientation, each of the sensors 1012-1 through 1012-5 generates a scan in a direction parallel to the length of the channel 1011A (i.e., orthogonal to the scans performed by the sensor 912 of the station 900). The sensor 1012 measurements are then processed by a depth analysis unit (e.g., the depth analysis unit 120), not shown in FIG. 10. The automated inspection station 1000 may be used with an external computing device or system (e.g., a laptop or desktop computer) or integrated processing hardware acting as the depth analysis unit, for example.

The automated inspection station 1000 has the advantage of being fast and mechanically simple (e.g., by not requiring that any sensor 1012 move laterally across the width of the channel 1011A). However, sensor size may necessitate a relatively large spacing between sensors 1012, which increases the risk of any given syringe 902 moving (e.g., rotating) between scans by different ones of the sensors 1012.

Figures 11A, 11B, 11C:
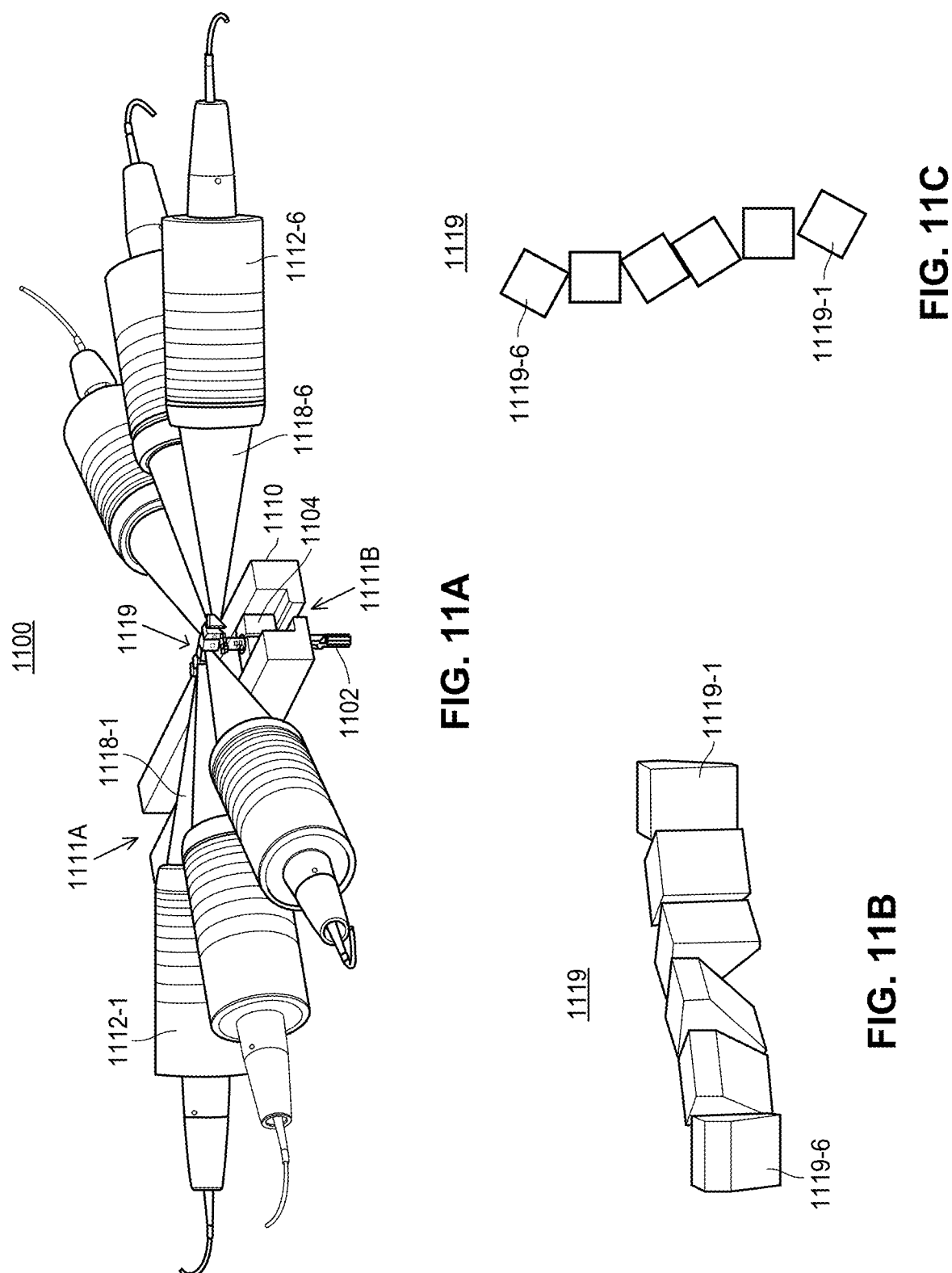
FIGS. 11A-11D are various perspective and overhead views of an alternative automated inspection station for inspecting syringes in a linear conveyance mechanism using multiple sensors.
Figure 11D:
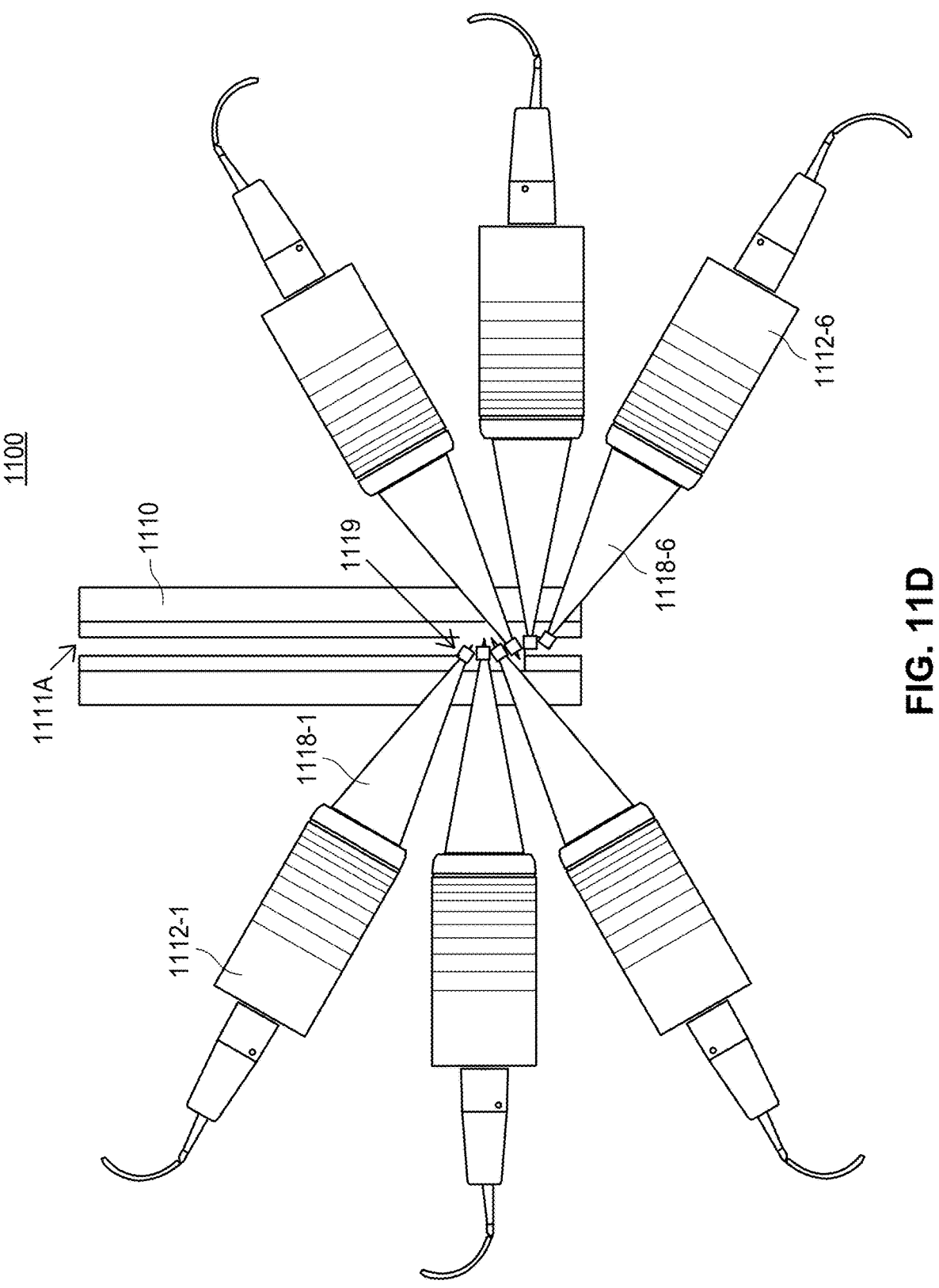

FIGS. 11A-11D are various perspective and overhead views of an alternative automated inspection station 1100 for inspecting syringes in a linear conveyance mechanism 1110 using multiple sensors 1112. As seen in FIG. 11A, the linear conveyance mechanism 1110 provides a straight, recessed channel 1111A in and along which a chuck 1104 can move (e.g., in response to a drive motor or pneumatic system not shown in FIG. 11A). The chuck 1104 (e.g., similar to chuck 904) is configured to hold a single syringe 1102, with a portion of the syringe barrel extending through a gap 1111B in the channel 1111A. A linear conveyor may move the chuck 1104 (and thus, the syringe 1102) along the channel 1111A. Like the station 1000 of FIG. 10, the linear conveyor may move the chuck 1104 and syringes 1102 continuously along the channel 1111A, rather than in discrete increments, and the sensors 1112 may all have fixed positions relative to the channel 1111A. Unlike the station 1000, however, the automated inspection station 1100 uses an optical system 1119 to alter the optical path between each sensor 1112 and a syringe 1102. Specifically, the optical system 1119 includes a set of mirrors 1119-1 through 1119-6, each shaped and arranged so as to complete an optical path between a respective one of the sensors 1112-1 through 1112-6 and the syringe 1102 being scanned. FIGS. 11B and 11C are perspective and overhead views, respectively, of the mirrors 1119-1 through 1119-6, while FIGS. 11A and 11D are perspective and overhead views, respectively, of the automated inspection station 1100 as a whole.

As seen in FIGS. 11A-11D, the mirrors 1119-1 through 1119-6 are angled and oriented such that each of the sensors 1112 scans the syringe 1102 at a different lateral offset along the width of the channel 1111A, and at a different position along the length of the channel 1111A. In this manner, the optical system 1119 allows the sensors 1112 to scan along different portions of each syringe 1102 (as in station 1000), but without the sensor size necessitating a large distance between subsequent scans by the different sensors 1112 (and thus, with less risk of a syringe 1102 rotating between scans by different sensors 1112).

The sensors 1112-1 through 1112-6 may be confocal chromatic sensors (as shown in FIG. 11A-11D, with light cones 1118-1 through 1118-6, respectively), or any other sensor type discussed herein. While six sensors 1112 and six respective mirrors 1119 are shown in FIG. 11, other embodiments may have more or fewer sensors and mirrors. The sensors 1112-1 through 1112-6 may operate sequentially as the chuck 1104 and syringe 1102 passes beneath each of the mirrors 1119-1 through 1119-6). Due to the movement of the chuck 1104 and syringe 1102 along the channel 1111A, each of the sensors 1112-1 through 1112-6 generates a scan in a direction parallel to the length of the channel 1111A (i.e., orthogonal to the scans performed by the sensor 912 of the station 900).

To properly direct the optical path between sensor 1112 and syringe 1102, each of the mirrors 1119-1 through 1119-6 may have one surface, within the optical path, that is at a 45 degree angle relative to the center/long axis of the syringe 1102, and also at a 45 degree angle relative to the optical axis of the respective sensor 1112. In other embodiments, other angles may be used (e.g., if any one or more of the sensors 1112 are not in a plane parallel to the plane of the syringe flanges). For example, additional sensors may be employed in a roughly spherical (or semi-spherical) arrangement around the chuck 1104, all aiming generally inwards toward the optical system 1119, in order to further increase throughput. The mirrors 1119-1 through 1119-6 are preferably designed so as to avoid substantially degradation of, or interference with, the optical signal between the syringe 1102 and sensor 1112. The optical system 1119 may include additional or alternative optics to further optimize the arrangement.

The sensor 1112 measurements are processed by a depth analysis unit (e.g., the depth analysis unit 120), not shown in FIG. 11. The automated inspection station 1100 may be used with an external computing device or system (e.g., a laptop or desktop computer) or integrated processing hardware acting as the depth analysis unit, for example.

Figures 12A, 12B, 12C:
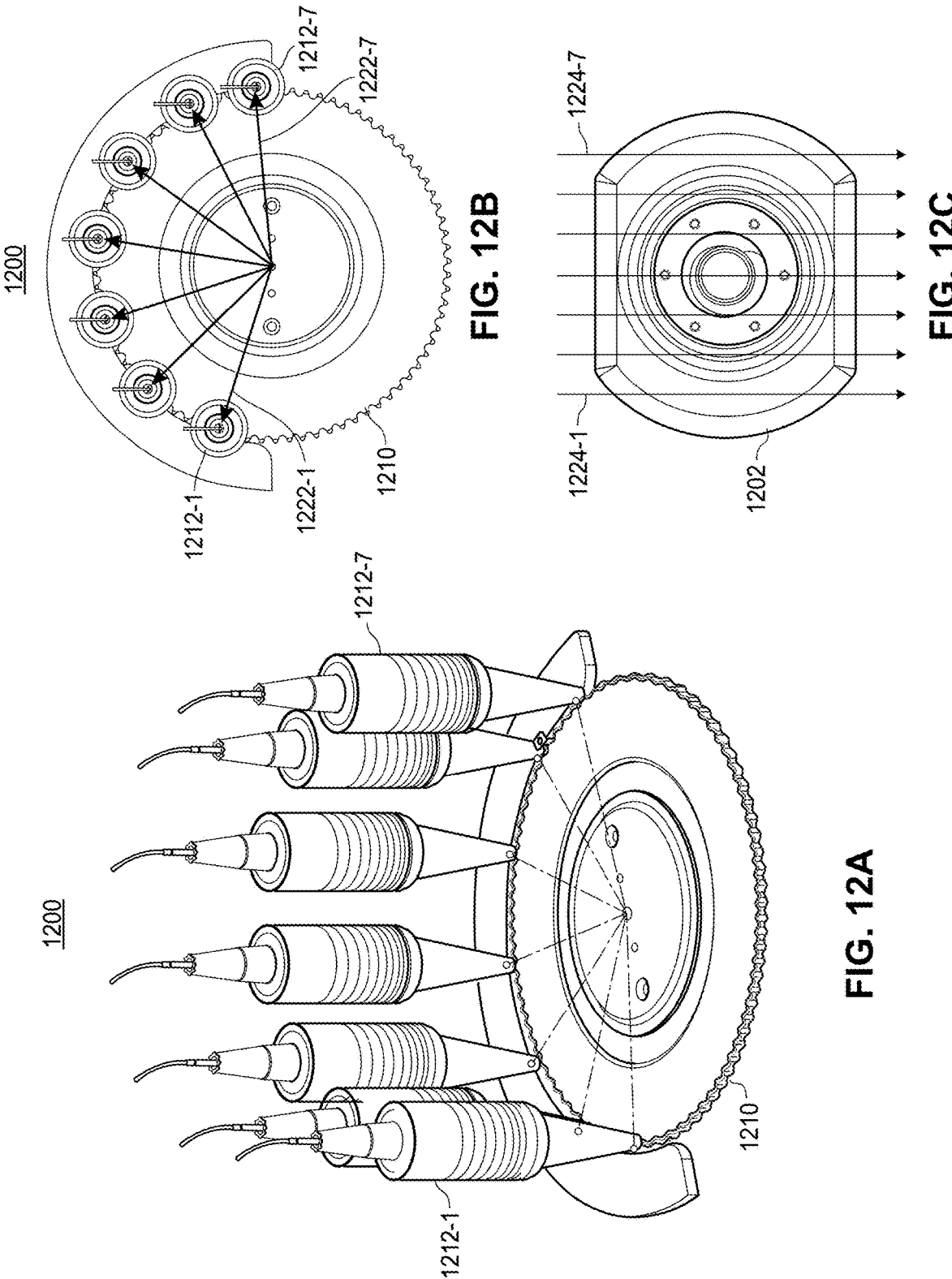
FIGS. 12A-12C depict an example automated inspection station in which multiple sensors are positioned along a star wheel at different radial offsets.

FIGS. 12A-12C depict an alternative embodiment of an automated inspection station 1200, in which multiple sensors 1212 (e.g., of the sensor system 112) are positioned at intervals over a periphery of a star wheel 1210, at different radial offsets 1222 relative to the center of the star wheel 1210. Star wheels are commonly used at the fill stage, and can also be used for combination device assembly lines in scenarios where plunger depth measurement is relevant at that stage. While star wheels can expose the side of the syringe for image capture (i.e., for machine vision techniques), some system geometries are not conducive to camera installation. In these cases, the proximal-end sensing techniques described herein may provide a viable alternative.

FIGS. 12A-12C show an embodiment in which there are seven confocal chromatic sensors 1212-1 through 1212-7 at seven different radial offsets 1222-1 through 1222-7. However, the automated inspection station 1200 may include more or fewer than seven sensors 1212, and some or all of the sensors 1212 may be of different types (e.g., single-depth-of-focus or ToF sensors). The radial offsets 1222-1 through 1222-7 may differ by some fraction of the width of a syringe 1202 (e.g., such that the scan lines are evenly distributed across at least the entire flange of each syringe 1202, regardless of flange rotation). While the rotation of the star wheel 1210 causes each scan line 1224 to be slightly arced, the resulting depth profiles can be treated as straight lines to a first approximation, so long as the radius of the star wheel 1210 is sufficiently large relative to the size of the syringe 1202. The depth analysis unit 120 may then synchronize the scans/profiles for the different sensors 1212, and calculate the plunger depth based on the synchronized profiles. The use of multiple sensors 1212 can improve the efficacy of the system by more precisely capturing the flange and plunger shape/orientation, without compromising system throughput. In some embodiments, the star wheel 1210 uses a pneumatic-based drive system (e.g., as part of the syringe conveyance mechanism 110), or other mechanism (e.g., a chuck similar to the chuck 904) in order to more firmly hold the syringes in place without allowing the syringes to rotate around their center axes.

A prototype station designed according to the principles and techniques disclosed herein exhibited high speed/throughput without sacrificing accuracy, and without requiring extra handling of the syringes (e.g., without removing the syringes from tubs). The prototype used a three-axis, TT-C3-4040 Cartesian robot (Intelligent Actuator, Inc.) to position an IFS2405-30 confocal chromatic sensor (Micro-Epsilon) over syringes in a syringe tub, with a confocal DT 2461 sensor controller (Micro-Epsilon) and Visual Studio 2017 control software (Microsoft).

Gage R&R (repeatability and reproducibility) studies were performed to assess the amount of variation in the measurements provided by the prototype station. One metric used was the precision-to-tolerance ratio (P/T or PTR), defined as:

$$PTR = \frac{k\sigma_g}{USL - LSL} \times 100\%,$$

where $\sigma_g$ is the measurement standard deviation. For this assessment, the constant k was set equal to 6, and USL (upper specification limit) minus LSL (lower specification limit) was set equal to 3 mm. For 10 sample syringes, and with some manual variation in how each syringe sits in its "nest" within the tub, a first run resulted in a PTR of 3.8%, and a second run resulted in a PTR of 3.7%. Generally, a PTR of 10% to 30% was considered "marginal" performance and a PTR under 10% was considered "good" performance. For the two runs, Gage R&R repeatability was 0.019 and 0.016, respectively, and Gage R&R reproducibility was 0.000 and 0.010, respectively (i.e., the prototype inspection station exhibited very good repeatability and reproducibility).

The prototype inspection station was largely insensitive to variations in flange orientation (i.e., variations in the amount of rotation of the asymmetrical flange around the axis of the syringe barrel). FIG. 13 is a table 1300 showing plunger depths (in mm) that the prototype inspection station calculated for 10 sample syringes across a range of different flange orientations (0 to 315 degrees at 45 degree increments). As seen in FIG. 13, for any given sample, the measurements varied by 0.1 mm or less. Even with this full range of flange orientations, PTR did not exceed 4.0%.

Figure 14:
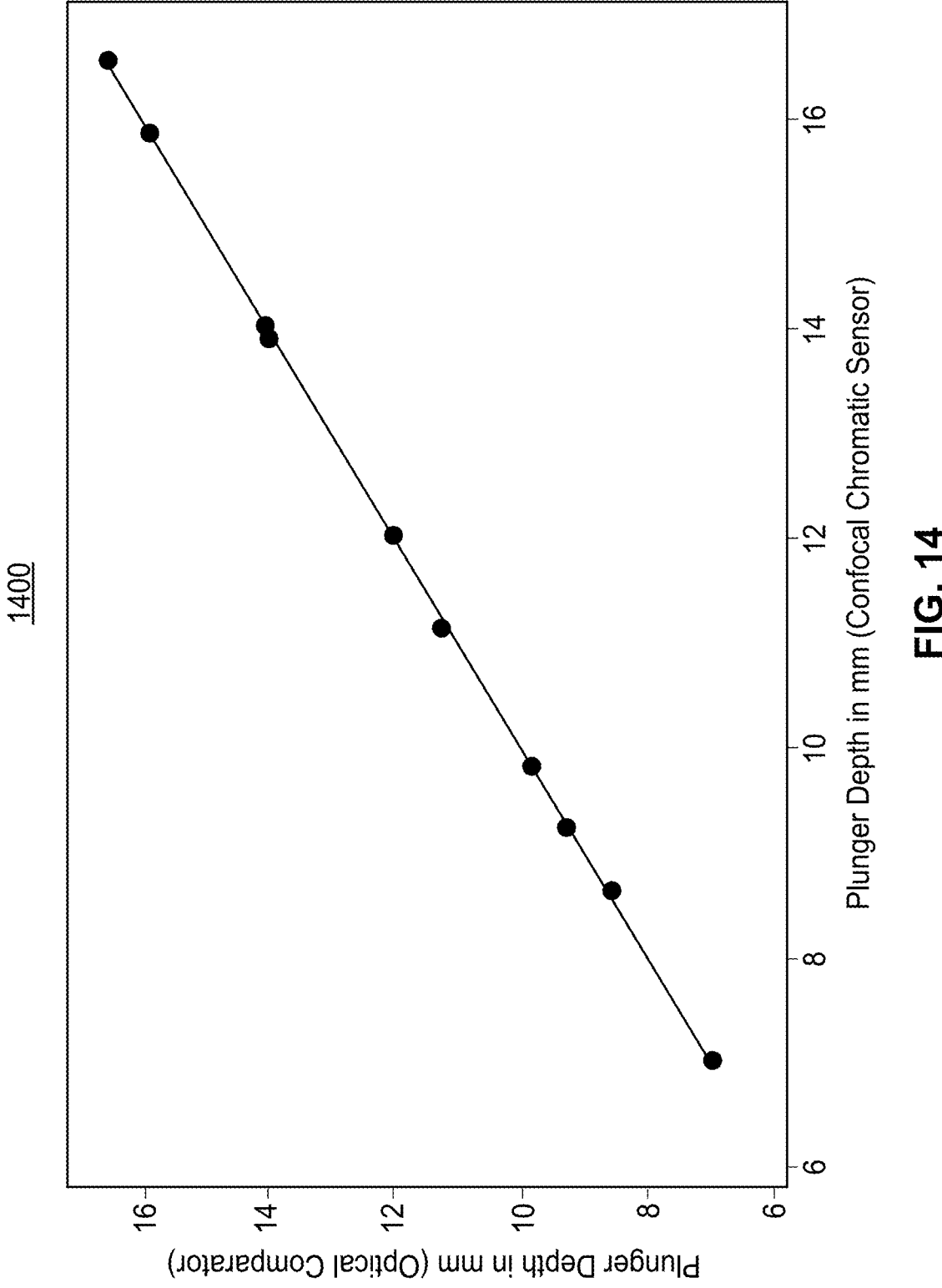
FIG. 14 is a plot comparing plunger depths determined using a confocal chromatic sensor with plunger depths determined using an optical comparator.

FIG. 14 is a plot 1000 comparing plunger depths determined using the confocal chromatic sensor prototype (x-axis) with plunger depths determined using a conventional optical comparator (y-axis). Both axes show the measured plunger depth in millimeters. As seen in FIG. 14, the prototype station reliably provided results very similar to the optical comparator. The prototype station, however, provided results at a much greater speed. Specifically, by capturing measurements at 70,000 samples per second (for a one-dimensional depth profile), the prototype station operated about ten times faster than optical comparators. A P-value for the confocal chromatic sensor prototype relative to the optical comparator was less than 0.001, indicating a high degree of statistical similarity. While there was a small, 30 micrometer bias between the two systems, this was statistically insignificant given that some of the optical comparator measurements exhibited normal human error. With the prototype, the element of human error was almost completely absent.

FIG. 15 is a flow diagram of an example method 1500 for automated inspection of plunger depths or, more generally, for automated inspection of distances between two portions of a syringe. The method 1500 may be implemented by an automated inspection system, such as the automated inspection station 100 of FIG. 1 or equipment that includes the automated inspection station 100.

At block 1502, a sensor system generates a plurality of syringe scans by scanning each of a plurality of syringes (e.g., syringes 102) from a proximal end perspective (e.g., while the syringes are held in an upright position by a tub, Rondo tray, star wheel holders, or another container or mechanism, or possibly while the syringes are held or supported horizontally on their sides, etc.). Block 1502 may be performed by the sensor system 112 (e.g., a sensor and sensor controller), for example, in a fill line, a product assembly process (e.g., in-line and prior to assembly), or in any other suitable process where the proximal end of each syringe is accessible for scanning. Each of the syringe scans is indicative of depth (distance) relative to a sensor of the sensor system, at each of a plurality of scan points within the scan, and/or along a scan line. The depth/distance corresponds to an optical path between the sensor and syringe, which may be a straight line or may be redirected one or more times by an optical system (e.g., by one or more mirrors such as in the optical system 1119). The sensor may be an optical sensor, such as a confocal chromatic sensor (e.g., sensor 512) or single-depth-of-focus sensor (e.g., sensor 560), for example. Alternatively, the sensor may be another suitable sensor type, such as a ToF sensor (e.g., a ToF camera). The sensor system may generate the syringe scans at a rate of at least 25,000 measurements per second (e.g., 70,000 measurements per second). The plurality of syringe scans may be one-dimensional or two-dimensional (e.g., a raster or snake scan), and may be discrete scans or all included within a single, continuous scan.

Block 1504 represents a process that is repeated for each of the plurality of syringes (e.g., for all syringes in a tub). Block 1504 may be performed by the depth analysis unit 120, for example. Within block 1504, at block 1506, the respective scan for the syringe is analyzed to determine two distances relative to the sensor (e.g., relative to the sensor head): a first distance to a first portion of the syringe (e.g., to the flange, or to a "marker" component that protrudes inward from the inner wall of the syringe barrel, etc.), and a second distance to a second portion of the syringe (e.g., to the plunger). For example, block 1506 may include analyzing a flange region of interest (ROI) within the syringe scan to determine the first distance (e.g., by determining an average distance to a proximal surface of the flange relative to the sensor), and analyzing a plunger ROI within the syringe scan to determine the second distance (e.g., by determining an average distance to a proximal surface of the plunger relative to the sensor, possibly after disregarding/discarding samples corresponding to dimples and/or beveled edges of the plunger).

Also within block 1504, at block 1508, a distance between the first and second portions (e.g., a depth of the plunger) of the syringe is calculated based on the first and second distances that were determined at block 1506. Block 1508 may include subtracting the first distance from the second distance, for example.

In some embodiments, block 1502 includes generating multiple scans using multiple sensors of the sensor system. For example, each scan may be generated using a sensor located at a different offset relative to each syringe (e.g., as shown in FIG. 10A-10D or 12A-12C). In these embodiments, block 1506 may include determining the first and second distance by analyzing all of the sensor scans (e.g., after synchronizing the measurement data from the various scans).

In some embodiments, the method 1500 includes one or more additional blocks, not shown in FIG. 15. For example, the method 1500 may include, before block 1502, using the sensor system to generate a preliminary scan of the syringe holder (e.g., tub), and determining positions at which the syringes are present within the syringe holder by analyzing the preliminary scan. As another example, the method 1500 may include, before block 1502, using the sensor system to generate one or more calibration scans at one or more positions having known distances relative to the sensor. As still another example, the method 1500 may include, after block 1508 and for each syringe, comparing the calculated distance between the first and second portions to a predetermined distance range to determine whether the calculated distance is within the predetermined distance range, and/or storing the calculated distance in a memory.

Embodiments of the disclosure relate to a non-transitory computer-readable storage medium having computer code thereon for performing various computer-implemented operations. The term "computer-readable storage medium" is used herein to include any medium that is capable of storing or encoding a sequence of instructions or computer codes for performing the operations, methodologies, and techniques described herein. The media and computer code may be those specially designed and constructed for the purposes of the embodiments of the disclosure, or they may be of the kind well known and available to those having skill in the computer software arts. Examples of computer-readable storage media include, but are not limited to: magnetic media such as hard disks, floppy disks, and magnetic tape; optical media such as CD-ROMs and holographic devices; magneto-optical media such as optical disks; and hardware devices that are specially configured to store and execute program code, such as ASICs, programmable logic devices ("PLDs"), and ROM and RAM devices.

Examples of computer code include machine code, such as produced by a compiler, and files containing higher-level code that are executed by a computer using an interpreter or a compiler. For example, an embodiment of the disclosure may be implemented using Java, C++, or other object-oriented programming language and development tools. Additional examples of computer code include encrypted code and compressed code. Moreover, an embodiment of the disclosure may be downloaded as a computer program product, which may be transferred from a remote computer (e.g., a server computer) to a requesting computer (e.g., a client computer or a different server computer) via a transmission channel. Another embodiment of the disclosure may be implemented in hardwired circuitry in place of, or in combination with, machine-executable software instructions.

As used herein, the singular terms "a," "an," and "the" may include plural referents, unless the context clearly dictates otherwise.

As used herein, the terms "connect," "connected," and "connection" refer to (and connections depicted in the drawings represent) an operational coupling or linking. Connected components can be directly or indirectly coupled to one another, for example, through another set of components.

As used herein, the terms "approximately," "substantially," "substantial" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, two numerical values can be deemed to be "substantially" the same if a difference between the values is less than or equal to ±10% of an average of the values, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified.

While the present disclosure has been described and illustrated with reference to specific embodiments thereof, these descriptions and illustrations do not limit the present disclosure. It should be understood by those skilled in the art that various changes may be made and equivalents may be substituted without departing from the true spirit and scope of the present disclosure as defined by the appended claims. The illustrations may not be necessarily drawn to scale. There may be distinctions between the artistic renditions in the present disclosure and the actual apparatus due to manufacturing processes, tolerances and/or other reasons. There may be other embodiments of the present disclosure which are not specifically illustrated. The specification (other than the claims) and drawings are to be regarded as illustrative rather than restrictive. Modifications may be made to adapt a particular situation, material, composition of matter, technique, or process to the objective, spirit and scope of the present disclosure. All such modifications are intended to be within the scope of the claims appended hereto. While the techniques disclosed herein have been described with reference to particular operations performed in a particular order, it will be understood that these operations may be combined, sub-divided, or re-ordered to form an equivalent technique without departing from the teachings of the present disclosure. Accordingly, unless specifically indicated herein, the order and grouping of the operations are not limitations of the present disclosure.

What is claimed:

1. An automated inspection system, comprising:
a sensor system including a sensor and configured to generate a plurality of syringe scans by scanning each of a plurality of syringes from a proximal end perspective, each of the plurality of syringe scans being indicative of distance relative to the sensor; and
one or more processors configured to, for each of the plurality of syringes,
analyze the respective syringe scan to determine (i) a first distance from the sensor to a first surface of the syringe and (ii) a second distance from the sensor to a second surface of the syringe, and
calculate a distance between the first surface and the second surface based on the first distance and the second distance.

2. The automated inspection system of claim 1, wherein the sensor is an optical sensor.

3. The automated inspection system of claim 2, wherein the optical sensor is a confocal chromatic sensor.

4. The automated inspection system of claim 2, wherein the optical sensor is a single-depth-of-focus sensor.

5. The automated inspection system of claim 1, wherein the sensor is a time-of-flight (ToF) sensor.

6. The automated inspection system of claim 1, wherein:
the second surface of the syringe is a surface of a plunger of the syringe; and
the first surface of the syringe is a surface of a flange of the syringe.

7. The automated inspection system of claim 6, wherein analyzing the respective syringe scan includes:
analyzing a flange region of interest (ROI) within the respective syringe scan to determine the first distance; and
analyzing a plunger ROI within the respective syringe scan to determine the second distance.

8. The automated inspection system of claim 1, wherein the sensor system is configured to generate a continuous scan that comprises the plurality of syringe scans.

9. The automated inspection system of claim 1, wherein each of the plurality of syringe scans is a one-dimensional scan.

10. The automated inspection system of claim 1, wherein each of the plurality of syringe scans is a two-dimensional scan.

11. The automated inspection system of claim 1, further comprising:
a sensor positioning mechanism configured to move the sensor,
wherein the sensor is a passive device configured to generate the plurality of syringe scans as the sensor positioning mechanism moves the sensor relative to the plurality of syringes.

12. The automated inspection system of claim 11, wherein:
the sensor is a single-depth-of-focus sensor; and
the single-depth-of-focus sensor is configured to generate the plurality of syringe scans as the sensor positioning mechanism additionally moves the single-depth-of-focus sensor towards and/or away from each syringe of the plurality of syringes.

13. The automated inspection system of claim 1, wherein the sensor system is configured to generate the plurality of syringe scans by scanning each of the plurality of syringes while the plurality of syringes are held in an upright position by a syringe holder.

14. The automated inspection system of claim 13, wherein:
the sensor system is further configured to generate a preliminary scan of the syringe holder prior to generating the plurality of syringe scans; and
the one or more processors are further configured to determine positions at which the plurality of syringes are present within the syringe holder by analyzing the preliminary scan.

15. The automated inspection system of claim 1, comprising:
a star wheel,
wherein the sensor system further includes one or more additional sensors each configured to generate a plurality of additional syringe scans by scanning each of the plurality of syringes,
wherein the sensor and each of the one or more additional sensors are offset from a center point of the star wheel by different radial distances, and
wherein the one or more processors are configured to, for each of the plurality of syringes, analyze the respective syringe scan and the respective one or more additional syringe scans to determine the first distance and the second distance.

16. The automated inspection system of claim 1, wherein the one or more processors are further configured to, for each of the plurality of syringes:
compare the calculated distance between the first surface and the second surface to a predetermined distance range to determine whether the calculated distance is within the predetermined distance range.

17. A method for automated inspection of syringes, the method comprising:
generating, by a sensor system that includes a sensor, a plurality of syringe scans by scanning each of a plurality of syringes from a proximal end perspective, each of the plurality of syringe scans being indicative of distance relative to the sensor; and
for each of the plurality of syringes,
analyzing, by one or more processors, the respective syringe scan to determine (i) a first distance from the sensor to a first surface of the syringe and (ii) a second distance from the sensor to a second surface of the syringe, and
calculating, by the one or more processors, a distance between the first surface and the second surface based on the first distance and the second distance.

18. The method of claim 17, wherein the sensor is a confocal chromatic sensor.

19. The method of claim 17, wherein the sensor is a single-depth-of-focus sensor.

20. The method of claim 17, wherein the second surface of the syringe is a surface of a plunger of the syringe, and wherein the first surface of the syringe is a surface of a flange of the syringe.

21. The method of claim 20, wherein analyzing the respective syringe scan includes:
analyzing a flange region of interest (ROI) within the respective syringe scan to determine the first distance; and
analyzing a plunger ROI within the respective syringe scan to determine the second distance.

22. The method of claim 17, wherein generating the plurality of syringe scans includes:
generating a continuous scan that comprises the plurality of syringe scans.

23. The method of claim 17, wherein generating the plurality of syringe scans includes generating a plurality of one-dimensional scans.

24. The method of claim 17, wherein generating the plurality of syringe scans includes generating a plurality of two-dimensional scans.

25. The method of claim 17, further comprising:

moving the sensor relative to the plurality of syringes while generating the plurality of syringe scans.

26. The method of claim 25, wherein:

the sensor is a single-depth-of-focus sensor; and moving the sensor relative to the plurality of syringes additionally includes moving the single-depth-of-focus sensor towards and/or away from each syringe of the plurality of syringes, while generating the plurality of syringe scans.

27. The method of claim 17, wherein generating the plurality of syringe scans includes scanning each of the plurality of syringes while the plurality of syringes are held in an upright position by a syringe holder.

28. The method of claim 27, further comprising:

prior to generating the plurality of syringe scans, generating, by the sensor system, a preliminary scan of the syringe holder; and determining positions at which the plurality of syringes are present within the syringe holder by analyzing the preliminary scan.

29. The method of claim 17, further comprising:

comparing, by the one or more processors, the calculated distance between the first surface and the second surface to a predetermined distance range to determine whether the calculated distance is within the predetermined distance range.

30. One or more tangible, non-transitory, computer-readable media storing instructions that, when executed by one or more processors, cause the one or more processors to, for each of a plurality of syringes:

analyze a respective one of a plurality of syringe scans generated from a proximal end perspective and by a sensor system to determine (i) a first distance from a sensor to a first surface of the syringe and (ii) a second distance from the sensor to a second surface of the syringe, the sensor system including the sensor, and each of the plurality of syringe scans being indicative of distance relative to the sensor; and calculate a distance between the first surface and the second surface based on the first distance and the second distance.

* * * * *